United States Patent
Lange et al.

(10) Patent No.: US 8,409,474 B2
(45) Date of Patent: Apr. 2, 2013

(54) USE OF POLYNUCLEAR PHENOLIC COMPOUNDS AS STABILISERS

(75) Inventors: Arno Lange, Bad Duerkheim (DE); Helmut Mach, Heidelberg (DE); Hans Peter Rath, Gruenstadt (DE); Dietmar Posselt, Heidelberg (DE)

(73) Assignee: BASF SE, Ludwigshafen (DE)

( * ) Notice: Subject to any disclaimer, the term of this patent is extended or adjusted under 35 U.S.C. 154(b) by 168 days.

(21) Appl. No.: 12/279,553

(22) PCT Filed: Feb. 21, 2007

(86) PCT No.: PCT/EP2007/051632
§ 371 (c)(1),
(2), (4) Date: Aug. 15, 2008

(87) PCT Pub. No.: WO2007/099048
PCT Pub. Date: Sep. 7, 2007

(65) Prior Publication Data
US 2009/0065744 A1    Mar. 12, 2009

(30) Foreign Application Priority Data
Feb. 27, 2006 (EP) .................... 06003970

(51) Int. Cl.
*C09K 15/00* (2006.01)
*C07C 211/00* (2006.01)
*C10L 1/22* (2006.01)
*C10L 1/183* (2006.01)

(52) U.S. Cl. ............ 252/404; 44/424; 44/450; 564/336; 564/367

(58) Field of Classification Search ............... 252/404; 544/90
See application file for complete search history.

(56) References Cited

U.S. PATENT DOCUMENTS

| | | | |
|---|---|---|---|
| 2,459,112 A | | 1/1949 | Oberright |
| 4,895,578 A | * | 1/1990 | Meyer et al. ............ 44/335 |
| 5,876,468 A | * | 3/1999 | Moreton ............... 44/415 |
| 6,323,270 B1 | | 11/2001 | Ishida |
| 2005/0274063 A1 | * | 12/2005 | Forester et al. .......... 44/331 |

FOREIGN PATENT DOCUMENTS

| | | |
|---|---|---|
| CA | 2 386 279 A1 | 4/2001 |
| CA | 2 386 281 A1 | 4/2001 |
| CA | 2386279 A * | 4/2001 |
| CA | 2 555 082 | 8/2005 |
| JP | 2003-255487 | 9/2003 |
| WO | WO 01/25293 A1 | 4/2001 |
| WO | WO 01/25294 A1 | 4/2001 |
| WO | WO 03/106595 A2 | 12/2003 |
| WO | WO 2005/073152 A2 | 8/2005 |

OTHER PUBLICATIONS

D. Jamois, et al. "Preparation of Amphiphilic Polyisobutylenes-b-polyethylenamines by Mannich Reaction. II. Study of Munnich Reaction on Model Systems", Journal of Polymer Science, Part A, Polymer Chemistry, vol. 31, pp. 1941-1958.

* cited by examiner

*Primary Examiner* — Peter F Godenschwager
(74) *Attorney, Agent, or Firm* — Oblon, Spivak, McClelland, Maier & Neustadt, L.L.P.

(57) ABSTRACT

The use of polycyclic phenolic compounds which have up to 20 benzene rings per molecule and are obtainable by reacting a tetrahydrobenzoxazine I

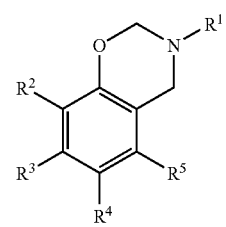

(I)

where $R^1$ is a hydrocarbyl radical and $R^2$, $R^3$, $R^4$ and $R^5$ are each independently hydrogen atoms, hydroxyl groups or hydrocarbyl radicals
with one or more of the same or different phenols II

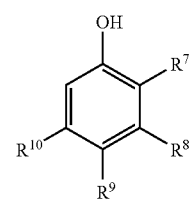

(II)

where $R^7$, $R^8$, $R^9$ and $R^{10}$ are each independently hydrogen atoms, hydroxyl groups or hydrocarbyl radicals,
and/or with one or more of the same or different tetrahydrobenzoxazines I,
with the proviso that at least one of the substituents has from 13 to 3000 carbon atoms and the remaining substituents, when they are hydrocarbyl radicals, have in each case from 1 to 20 carbon atoms
as stabilizers for stabilizing inanimate organic material against the action of light, oxygen and heat.

12 Claims, No Drawings

USE OF POLYNUCLEAR PHENOLIC COMPOUNDS AS STABILISERS

The present invention relates to the use of specific polycyclic phenolic compounds as stabilizers for stabilizing inanimate organic material against the action of light, oxygen and heat, especially in turbine fuels (jet fuels) and lubricant compositions. The present invention further relates to a turbine fuel composition and to an additive concentrate for turbine fuels, which comprise these polycyclic phenolic compounds. The present invention further relates to a lubricant composition which comprises these polycyclic phenolic compounds. The present invention further relates to a process for preparing these polycyclic phenolic compounds. Since some of these polycyclic phenolic compounds are novel substances, the present invention also relates to these novel substances themselves.

The mechanical, chemical and/or esthetic properties of inanimate organic material, for example of plastics and coatings, but also of mineral oil products and fuels, are known to be impaired by the action of light, oxygen and heat. This impairment is exhibited typically in the form of yellowing, discoloration, crack formation or embrittlement of the material. Stabilizers or stabilizer compositions with which improved protection against such impairment of organic material by light, oxygen and heat can be achieved are already known.

For instance, WO 05/073152 (1) describes 2-alkylpolyisobutenylphenols and their Mannich adducts as antioxidants for stabilizing inanimate organic material against the action of light, oxygen and heat. Other materials to be stabilized include fuels such as gasoline fuels, diesel fuels and turbine fuels, and also lubricant compositions. In turbine fuels, these 2-alkylpolyisobutenylphenols and their Mannich adducts bring about an improvement in the thermal stability and a reduction in the deposits in the fuel circuit and combustion system of the turbines.

WO 03/106595 (2) also discloses, as well as hydrocarbyl-substituted succinic acid derivatives and polyalkenylthiophosphonate esters, Mannich adducts made from hydrocarbyl-substituted phenols, an aldehyde and an amine as additives for turbine fuels (jet fuels) for improving the thermal stability and for reducing deposits.

Tetrahydrobenzoxazines having one benzene ring are known as additives for fuel and lubricant compositions. For instance, WO 01/25293 (3) and WO 01/25294 (4) disclose such tetrahydrobenzoxazines with relatively long-chain radicals such as polyisobutenyl radicals which reside on the benzene ring as substituents as gasoline fuel detergents which clean the valves and keep the valves clean. According to the preparation processes mentioned in (3) and (4), these tetrahydrobenzoxazines are obtained as mixtures with the corresponding open-chain Mannich adducts of the parent phenol and are also used thus in the gasoline fuels.

In Journal of Polymer Science, Part A, Polymer Chemistry, Vol. 31, page 1941-1958 (5), D. Jamois, M. Tessier and E. Maréchal describe preparation processes for polyisobutene-b-polyethyleneamines which are suitable as sludge dispersants in engine oils. The compounds prepared by these authors also include bicyclic phenolic compounds which are joined by a —$CH_2$—$N(C_{12}H_{25})$—$CH_2$— bridge via the particular ortho positions of the two phenol rings.

U.S. Pat. No. 6,323,270 B1 (6) discloses oligomers or polymers of tetrahydrobenzoxazines which may bear, on the nitrogen atom and/or on the benzene ring, alkyl groups having from 1 to 10 carbon atoms or aryl groups, alkylaryl groups or arylalkyl groups having in each case from 6 to 20 carbon atoms as substituents. The precise chemical structure of such tetrahydrobenzoxazine oligomers or polymers is not specified. These tetrahydrobenzoxazine oligomers or polymers are suitable for producing brake linings for aircraft, ceramic articles, packaging materials, coatings, adhesives and composite materials.

JP 2003-255 487 A (7) discloses polymeric polycyclic phenolic compounds which are joined in each case by —$CH_2$—$N(C_1$-$C_{25}$-alkyl)-$CH_2$— bridges or —$CH_2$—N(phenyl)-$CH_2$-bridges via the ortho positions of the phenol rings. The phenol rings themselves may also be substituted by $C_1$-$C_{25}$-alkyl radicals. The number of phenol rings in the polymer molecules is specified as from 2 to 1002. Specific examples mentioned of the $C_1$-$C_{25}$-alkyl radicals which occur are methyl, ethyl, butyl, octyl and dodecyl. Substituents which have an oligomeric or polymeric distribution are not mentioned. These polymeric polycyclic phenolic compounds are recommended as a photothermographic image-generating material.

Especially for the mineral oil products and fuels sector, there is a need for stabilizers and antioxidants with improved protective action against the impairment of the material properties by light, oxygen and heat. For turbine fuels (jet fuels) in particular, which are exposed to extreme thermal stress in the course of and before the combustion operation in turbines, for example in aviation turbines, novel improved stabilizers are being sought. In the turbines, these should simultaneously also reduce deposits in the fuel circuit and in the combustion system by virtue of their mode of action as antioxidants and/or dispersants. Furthermore, new improved stabilizers are being sought for lubricant compositions, which in particular offer improved protection against oxidation and aging behavior and/or improved shear stability.

It was therefore an object of the invention to provide stabilizers with improved stabilization of inanimate organic material, especially of mineral oil products and fuels, in particular of turbine fuel and of lubricant compositions, against the action of light, oxygen and heat.

Accordingly, the use of polycyclic phenolic compounds which have up to 20 benzene rings per molecule and are obtainable by reacting a tetrahydrobenzoxazine of the general formula I

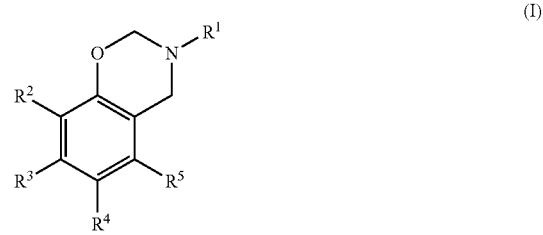

in which the substituent $R^1$ is a hydrocarbyl radical which has from 1 to 3000 carbon atoms and may be interrupted by one or more heteroatoms from the group of O and S and/or by one or more $NR^6$ moieties, where $R^6$ is a hydrogen atom or a $C_1$- to $C_4$-alkyl radical, and in which the substituents $R^2$, $R^3$, $R^4$ and $R^5$ are each independently hydrogen atoms, hydroxyl groups or hydrocarbyl radicals which have in each case from 1 to 3000 carbon atoms and may be interrupted by one or more heteroatoms from the group of O and S and/or by one or more $NR^6$ moieties, where $R^6$ is as defined above, with one or more of the same or different phenols of the general formula II

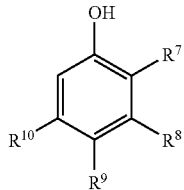

in which the substituents $R^7$, $R^8$, $R^9$ and $R^{10}$ are each independently hydrogen atoms, hydroxyl groups or hydrocarbyl radicals which have in each case from 1 to 3000 carbon atoms and may be interrupted by one or more heteroatoms from the group of O and S and/or by one or more $NR^6$ moieties, where $R^6$ is as defined above, and/or with one or more of the same or different tetrahydrobenzoxazines of the general formula I, where the substituent $R^4$ may also be a radical of the formula Z and the substituent $R^9$ may also be a radical of the formula Z'

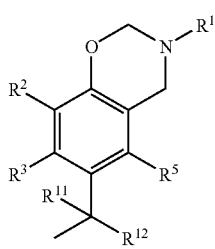

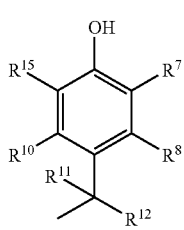

in which the substituents $R^1$, $R^2$, $R^3$, $R^5$, $R^7$, $R^8$ and $R^{10}$ are each as defined above, the substituent $R^7$ may also be a radical derived from a tetrahydrobenzoxazine of the general formula I, the substituent $R^{15}$ is hydrogen or a radical derived from a tetrahydrobenzoxazine of the general formula I, and the substituents $R^{11}$ and $R^{12}$ may be the same or different and are each hydrogen or a $C_1$- to $C_{10}$-alkyl radical, and in which the substituents $R^2$ and $R^3$ or $R^3$ and $R^4$ or $R^4$ and $R^5$, together with the substructure —O—$CH_2$—$NR^{13}$—$CH_2$— attached to the benzene ring, may also form a second tetrahydrooxazine ring, or the substituents $R^2$ and $R^3$ and $R^4$ and $R^5$, together with the substructures —O—$CH_2$—$NR^{13}$—$CH_2$— and —O—$CH_2$—$NR^{14}$—$CH_2$— attached to the benzene ring, may also form a second and a third tetrahydrooxazine ring, where $R^{13}$ and $R^{14}$ are each independently hydrocarbyl radicals which have in each case from 1 to 3000 carbon atoms and may be interrupted by one or more heteroatoms from the group of O and S and/or by one or more $NR^6$ moieties, where $R^6$ is as defined above, with the proviso that at least one of the substituents $R^1$, $R^2$, $R^3$, $R^4$, $R^5$, $R^7$, $R^8$, $R^9$, $R^{10}$, $R^{13}$ or $R^{14}$ has from 13 to 3000 carbon atoms, and the remaining substituents from the group of $R^1$, $R^2$, $R^3$, $R^4$, $R^5$, $R^7$, $R^8$, $R^9$, $R^{10}$, $R^{13}$ or $R^{14}$, when they are hydrocarbyl radicals, each have from 1 to 20 carbon atoms as stabilizers for stabilizing inanimate organic material against the action of light, oxygen and heat has been found.

The structural peculiarity of the polycyclic phenolic compounds to be used in accordance with the invention is that they comprise at least one relatively long-chain hydrocarbyl radical having from 13 to 3000 carbon atoms as one of the substituents $R^1$, $R^2$, $R^3$, $R^4$, $R^5$, $R^7$, $R^8$, $R^9$, $R^{10}$, $R^{13}$ or $R^{14}$ which stem from the tetrahydrobenzoxazines I or the phenols II used. In a preferred embodiment, this relatively long-chain hydrocarbyl radical having from 13 to 3000 carbon atoms is a polyisobutenyl radical. In a further embodiment, the relatively long-chain hydrocarbyl radical mentioned may also be a $C_{16}$- to $C_{20}$-alkyl or -alkenyl radical. In particular, this relatively long-chain hydrocarbyl radical, which is preferably a polyisobutenyl radical, is present on an oxazine ring or on a benzene ring in ortho or preferably in para position to the phenolic hydroxyl group, i.e. it occurs as substituent $R^1$ or $R^2$ or $R^4$ or $R^7$ or $R^9$ or $R^{13}$ or $R^{14}$. This relatively long-chain hydrocarbyl radical which is preferably a polyisobutenyl radical comprises preferably from 21 to 3000 or preferably from 21 to 1000, especially from 26 to 3000 or especially from 26 to 500, in particular from 30 to 3000 or in particular from 30 to 250 carbon atoms. In the case of polyisobutenyl radicals, they have number-average molecular weights $M_n$ of from 183 to 42 000, preferably from 500 to 15 000, especially from 700 to 7000, in particular from 900 to 3000, most preferably from 900 to 1100.

Suitable $C_{16}$- to $C_{20}$-alkyl or -alkenyl radicals are appropriately the radicals of corresponding saturated or unsaturated fatty alcohols having from 16 to 20 carbon atoms. Mention should be made here in particular of n-hexadecyl (palmityl), n-octadecyl (stearyl), n-eicosyl, oleyl, linolyl and linolenyl, which usually occur as technical mixtures with one another owing to their natural origin.

The relatively long-chain hydrocarbyl radical having from 13 to 3000 carbon atoms mentioned may also occur more than once, for example twice or three times, in the polycyclic phenolic compounds. In a preferred embodiment, one or two polyisobutenyl radicals having a particular number-average molecular weight $M_n$ of from 183 to 42 000 occur in the molecule as substituent $R^1$ and/or $R^2$ and/or $R^4$ and/or $R^7$ and/or $R^9$ and/or $R^{13}$ and/or $R^{14}$.

The remaining substituents from the group of $R^1$, $R^2$, $R^3$, $R^4$, $R^5$, $R^7$, $R^8$, $R^9$, $R^{10}$, $R^{13}$ or $R^{14}$ which are not substituents having from 13 to 3000 carbon atoms or polyisobutenyl radicals having a number-average molecular weight $M_n$ of from 183 to 42 000 are each independently hydrogen atoms, hydroxyl groups or, when they are hydrocarbyl radicals, usually relatively short-chain hydrocarbyl radicals having from 1 to 20, preferably from 1 to 12, in particular from 1 to 8, most preferably linear or branched $C_1$- to $C_4$-alkyl radicals. Typical examples of the latter are methyl, ethyl, n-propyl, isopropyl, n-butyl, 2-butyl, sec-butyl and tert-butyl. Very particular preference is given here to methyl radicals and tert-butyl radicals.

Polycyclic phenolic compounds tetrahydrobenzoxazines I to be used with preference in accordance with the invention are also those in which the substituents $R^2$ and/or $R^4$ and/or $R^7$ and/or $R^9$ which stem from the tetrahydrobenzoxazines I or phenols II used, when they are relatively short-chain hydrocarbyl radicals, are linear or branched $C_1$- to $C_4$-alkyl radicals, especially methyl radicals and/or tert-butyl radicals. Of course, such substitution patterns are only possible for tetrahydrobenzoxazines I having a total of one or two tetrahydrooxazine ring systems.

In the radical of the formula Z or Z', the substituents $R^{11}$ and $R^{12}$ are preferably each hydrogen and/or linear or branched $C_1$- to $C_4$-alkyl radicals, in particular methyl radicals. The compounds I and II having a Z or Z' radical, in which $R^{11}=R^{12}=$methyl, derive from bisphenol A [2,2-bis(4-hydroxyphenyl)propane]. As a result of the preparation, compounds I having a Z radical and compounds I having the corresponding Z' radical may also be present as mixtures.

Hydrocarbyl radicals having from 1 to 3000 or from 13 to 3000 carbon atoms for the substituents $R^1, R^2, R^3, R^4, R^5, R^7, R^8, R^9, R^{10}, R^{13}$ and $R^{14}$ should be understood here to mean pure hydrocarbon radicals of any structure, which, by definition, may also be interrupted by one or more heteroatoms from the group of O and S and/or by one or more $NR^6$ moieties. A typical hydrocarbyl radical interrupted by an $NR^6$ moiety derives from 3-(dimethylamino)propylamine. In particular, hydrocarbyl radicals are alkyl, alkenyl, cycloalkyl, aryl, alkylaryl, alkenylaryl or arylalkyl radicals.

Interruptions in the hydrocarbyl radical by $NR^6$ moieties also mean those radicals in which the $NR^6$ moieties have been inserted formally into a C—H bond at the end, i.e., for example, substituents $R^1, R^2, R^3, R^4, R^5, R^7, R^8, R^9, R^{10}, R^{13}$ and $R^{14}$ with an $NH_2$ end group. Such hydrocarbyl radicals derive, for example, from polyamines such as ethylenediamine, diethylenetriamine, triethylenetetramine, tetraethylenepentamine, etc., in which one of the terminal nitrogen atoms is the nitrogen atom in the oxazine ring.

The term "alkyl" comprises straight-chain and branched alkyl groups. Examples of alkyl groups are, in addition to the methyl, ethyl, n-propyl, isopropyl, n-butyl, 2-butyl, sec-butyl and tert-butyl radicals already mentioned above, in particular also n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, n-nonyl, n-decyl, n-dodecyl, n-tridecyl, isotridecyl, n-tetradecyl (myristyl), n-hexadecyl (palmityl), n-octadecyl (stearyl), and n-eicosyl.

Examples of alkenyl radicals are vinyl, 1-propenyl, 2-propenyl, oleyl, linolyl and linolenyl.

Examples of cycloalkyl radicals are $C_5$- to $C_7$-cycloalkyl groups such as cyclopentyl, cyclohexyl and cycloheptyl, which may also be substituted by alkyl groups, for example methyl radicals.

The term "aryl" comprises monocyclic, bicyclic, tricyclic and higher polycyclic aromatic hydrocarbon radicals. In the case of substitution by the alkyl and/or alkenyl radicals, for example those mentioned above, to give alkylaryl or alkenylaryl radicals, these aryl radicals may also bear 1, 2, 3, 4 or 5, preferably 1, 2 or 3 substituents. Typical examples are phenyl, tolyl, xylyl, mesityl, naphthyl, fluorenyl, anthracenyl, phenanthrenyl, naphthacenyl and styryl. A typical example of an arylalkyl radical is benzyl.

When the relatively long-chain hydrocarbyl radical having from 13 to 3000 carbon atoms is a polyisobutenyl radical, it may be based in principle on any common and commercially available polyisobutene, which is introduced in a suitable manner into the synthesis of the tetrahydrobenzoxazines 1. Such a polyisobutene has a number-average molecular weight $M_n$ of at least 183. Preference is given to polyisobutenes having a number-average molecular weight $M_n$ in the range from 183 to 42 000, more preferably from 500 to 15 000, in particular from 700 to 7000, especially from 900 to 3000 and most preferably from 900 to 1100. In the context of the present invention, the term "polyisobutene" also includes oligomeric isobutenes such as dimeric, trimeric, tetrameric, pentameric, hexameric and heptameric isobutene.

The polyisobutenyl radicals incorporated into the polycyclic phenolic compounds used in accordance with the invention preferably derive from so-called "reactive" polyisobutene. Reactive polyisobutenes differ from the conventional polyisobutenes by the content of terminal double bonds, i.e. of vinylidene double bonds [—CH—C$(CH_3)$=$CH_2$] (α-olefin) or vinyl double bonds [—CH=C$(CH_3)_2$] (β-olefin). For instance, reactive polyisobutenes comprise at least 50 mol % of terminal double bonds, based on the total number of polyisobutene macromolecules. Particular preference is given to polyisobutenes having at least 60 mol % and in particular having at least 80 mol % of terminal double bonds, based on the total number of polyisobutene macromolecules. Moreover, the essentially homopolymeric polyisobutenyl radicals have uniform polymer structures. In the context of the present invention, this is understood to mean polyisobutene systems which are formed to an extent of at least 85% by weight, preferably to an extent of at least 90% by weight, more preferably to an extent of at least 95% by weight and in particular to an extent of at least 99% by weight from isobutene units of the repeat unit [—$CH_2C(CH_3)_2$—].

A further preferred feature of the polyisobutenes which may be the parent molecules of the polycyclic phenolic compounds used in accordance with the invention is that they are terminated by a tert-butyl group [—$CH_2C(CH_3)_3$] to an extent of at least 15% by weight, especially to an extent of at least 50% by weight, in particular to an extent of at least 80% by weight.

Moreover, the polyisobutenes which preferably serve as the basis for the tetrahydrobenzoxazines I or phenols II used as the starting material for the polycyclic phenolic compounds used in accordance with the invention preferably have a polydispersity index (PDI) of from 1.05 to 10, preferably from 1.05 to 3.0, in particular from 1.05 to 2.0. Polydispersity is understood to mean the quotient of weight-average molecular weight $M_w$ and number-average molecular weight $M_n$ (PDI=$M_w/M_n$). In a preferred embodiment, the mean polydispersity index PDI for the polyisobutenyl radicals in the polycyclic phenolic compounds is at most 5 times, preferably at most 3 times, especially at most 2 times, in particular at most 1.5 times, the mean polydispersity index PDI for the polyisobutenyl radicals in the parent tetrahydrobenzoxazines I and/or phenols II.

In the context of the present invention, the polyisobutenes preferably serving as the basis of the tetrahydrobenzoxazines I or phenols II are also understood to mean all polymers which are obtainable by cationic polymerization and comprise, in copolymerized form, preferably at least 60% by weight of isobutene, more preferably at least 80% by weight, in particular at least 90% by weight and especially at least 95% by weight of isobutene. In addition, the polyisobutenes may comprise, in copolymerized form, further butene isomers such as 1- or 2-butene, and also different olefinically unsaturated monomers which are copolymerizable with isobutene under cationic polymerization conditions.

Suitable isobutene feedstocks for the preparation of polyisobutenes which can serve as the basis of the tetrahydrobenzoxazines I or phenols II are accordingly both isobutene itself and isobutenic $C_4$ hydrocarbon streams, for example $C_4$ raffinates, $C_4$ cuts from isobutene dehydrogenation, $C_4$ cuts from steamcrackers, FCC crackers (FCC: Fluid Catalyzed Cracking), provided that they have been substantially freed of 1,3-butadiene present therein. Particularly suitable $C_4$ hydrocarbon streams comprise generally less than 500 ppm, preferably less than 200 ppm of butadiene. When $C_4$ cuts are used as the starting material, the hydrocarbons other than isobutene assume the role of an inert solvent.

Useful monomers copolymerizable with isobutene include vinylaromatics such as styrene and a-methylstyrene, $C_1$-$C_4$-alkylstyrenes such as 2-, 3- and 4-methylstyrene, and also 4-tert-butylstyrene, isoolefins having from 5 to 10 carbon atoms, such as 2-methylbutene-1,2-methylpentene-1,2-methylhexene-1,2-ethylpentene-1,2-ethylhexene-1 and 2-propylheptene-1.

Typical polyisobutenes which can serve as the basis of the tetrahydrobenzoxazines I or phenols II are, for example, the Glissopal® brands from BASF Aktiengesellschaft, e.g. Glissopal 550, Glissopal 1000 and Glissopal 2300, and also the Oppanol® brands from BASF Aktiengesellschaft, e.g. Oppanol B10, B12 and B15.

In addition to polyisobutenyl radicals, it is also possible for the relatively long-chain hydrocarbyl radicals which occur to include those which derive from oligomers or polymers of $C_2$- to $C_{12}$-olefins and have an average of from 13 to 3000 carbon atoms. Such usually polydisperse hydrocarbyl radicals with polymeric distribution are, for example, those which derive from ethylene, propylene, butene, styrene, methylstyrene, hexene-1, octene-1, decene-1 or dodecene-1. They may be homo- or copolymer radicals. Their number-average molecular weight $M_n$ is at least 183; their polydispersity index PDI is typically from 1.05 to 10. In the case of low molecular weight radicals where $M_n$ is from 183 to approx. 500, they may also be present in monodisperse form.

In a preferred embodiment, the polycyclic phenolic compounds used in accordance with the invention have a mean molecular weight $M_n$ of from 411 to 25 000. For example, the molecular weight $M_n$ of 411 represents the smallest representatives of the polycyclic phenolic compounds in the context of the present invention, specifically bis-(ortho- or para-hydroxybenzyl)tridecylamine. Particularly preferred ranges for $M_n$ are from 523 to 25 000 or from 523 to 17 000, especially from 593 to 25 000 or from 593 to 10 000, in particular from 649 to 25 000 or from 649 to 5000.

Examples of typical polycyclic phenolic compounds in the context of the present invention are as follows, where "PIB" denotes a polyisobutenyl radical derived from a high-reactivity polyisobutene ($M_n$ 1000):

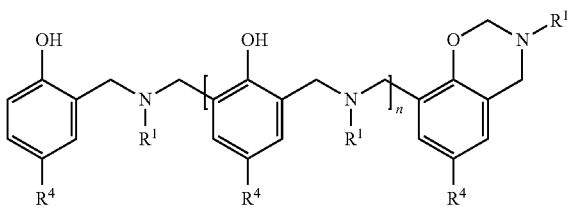

(IIIa) n=0, $R^1$=PIB, $R^4$=H
(IIIb) n=0, $R^1$=methyl, $R^4$=PIB
(IIIc) n=0, $R^1$=PIB, $R^4$=tert-butyl
(IIId) n=1, $R^1$=PIB, $R^4$=H
(IIIe) n=1, $R^1$=methyl, $R^4$=PIB
(IIIf) n=1, $R^1$=PIB, $R^4$=tert-butyl
(IIIg) n=2, $R^1$=PIB, $R^4$=H
(IIIh) n=2, $R^1$=methyl, $R^4$=PIB
(IIIi) n=2, $R^1$=PIB, $R^4$=tert-butyl
(IIIj) n=3, $R^1$=PIB, $R^4$=H
(IIIk) n=3, $R^1$=methyl, $R^4$=PIB
(IIIl) n=3, $R^1$=PIB, $R^4$=tert-butyl
(IIIm) n=4, $R^1$=PIB, $R^4$=H
(IIIn) n=4, $R^1$=methyl, $R^4$=PIB
(IIIo) n=4, $R^1$=PIB, $R^4$=tert-butyl
(IIIp) n=5, $R^1$=PIB, $R^4$=H
(IIIq) n=5, $R^1$=methyl, $R^4$=PIB
(IIIr) n=5, $R^1$=PIB, $R^4$=tert-butyl
(IIIs) n=6, $R^1$=PIB, $R^4$=H
(IIIt) n=6, $R^1$=methyl, $R^4$=PIB
(IIIu) n=6, $R^1$=PIB, $R^4$=tert-butyl
(IIIv) n=1, $R^1$=methyl,
  1 $R^4$ radical=PIB, 2 $R^4$ radicals=tert-butyl
(IIIw) n=8, $R^1$=methyl,
  1 $R^4$ radical=PIB, 9 $R^4$ radicals=tert-butyl

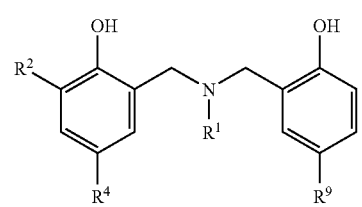

(IVa) $R^1$=methyl, $R^2$=H, $R^4$=tert-butyl, $R^9$=PIB
(IVb) $R^1$=methyl, $R^2$=$R^4$=tert-butyl, $R^9$=PIB
(IVc) $R^1$=PIB, $R^2$=$R^4$=tert-butyl, $R^9$=H
(IVd) $R^1$=PIB, $R^2$=$R^4$=$R^9$=H
(IVe) $R^1$=PIB, $R^2$=$R^4$=H, $R^9$=tert-butyl
(IVf) $R^1$=PIB, $R^2$=H, $R^4$=tert-butyl, $R^9$=PIB
(IVg) $R^1$=PIB, $R^2$=$R^4$=tert-butyl, $R^9$=PIB
(IVh) $R^1$=PIB, $R^2$=$R^4$=H, $R^9$=

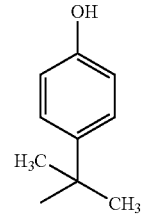

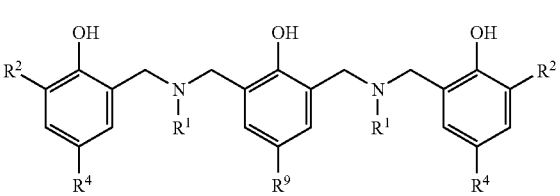

(Va) $R^1$=methyl, $R^2$=$R^4$=H, $R^9$=PIB
(Vb) $R^1$=methyl, $R^2$=$R^4$=tert-butyl, $R^9$=PIB
(Vc) $R^1$=methyl, $R^2$=tert-butyl, $R^4$=methyl, $R^9$=PIB
(Vd) $R^1$=$R^2$=methyl, $R^4$=tert-butyl, $R^9$=PIB
(Ve) $R^1$=3-(dimethylamino)propyl, $R^2$=$R^4$=tert-butyl, $R^9$=PIB
(Vf) $R^1$=PIB, $R^2$=$R^4$=$R^9$=H
(Vg) $R^1$=PIB, $R^2$=$R^4$=H, $R^9$=tert-butyl
(Vh) $R^1$=PIB, $R^2$=$R^4$=tert-butyl, $R^9$=H (Vi) R$^1$=PIB, R$^2$=H, R$^4$=R$^9$=tert-butyl (Vj) R$^1$=PIB, R$^2$=R$^4$=R$^9$=tert-butyl (Vk) R$^1$=PIB, R$^2$=R$^4$=H, R$^9$=PIB (Vm) R$^1$=PIB, R$^2$=R$^4$=H, R$^9$=

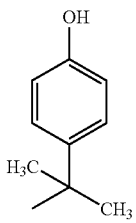

(Vn) R$^1$=3-(dimethylamino)propyl, R$^2$=tert-butyl, R$^4$=methyl, R$^9$=PIB

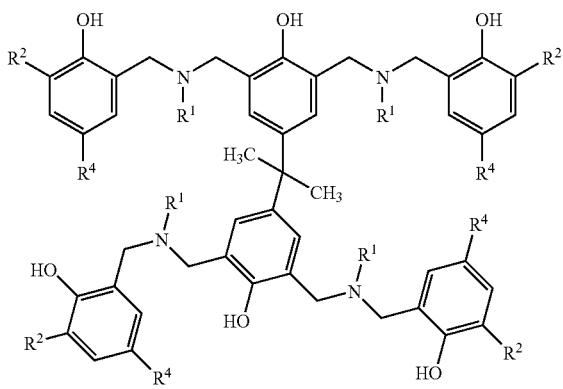

(VIa) R$^1$=methyl, R$^2$=tert-butyl, 3 R$^4$ radicals=tert-butyl, 1 R$^4$ radical =PIB (VIb) R$^1$=methyl, R$^2$=tert-butyl, 3 R$^4$ radicals=methyl, 1 R$^4$ radical=PIB (VIc) R$^1$=methyl, 3 R$^2$ radicals=tert-butyl, 1 R$^2$ radical=H. 3 R$^4$ radicals=tert-butyl, 1 R$^4$ radical (on the benzene ring when R$^2$=H)=PIB The polycyclic phenolic compounds described are used in accordance with the present invention as stabilizers for stabilizing inanimate organic material against the action of light, oxygen and heat. This is understood to mean in particular their mode of action as antioxidants in the conventional sense. To this end, these compounds are incorporated into the material to be stabilized during or after its production and distributed as homogeneously as possible. The concentration of these compounds in the organic material to be stabilized is generally from 0.0001 to 5% by weight, preferably from 0.001 to 5% by weight, in particular from 0.01 to 2% by weight, especially from 0.05 to 1% by weight, based on the organic material.

Inanimate organic material is understood to mean, for example, cosmetic preparations such as ointments and lotions, medicament formulations such as pills and suppositories, photographic recording materials, especially photographic emulsions, paints and plastics. They further include especially mineral oil products and fuels, for example diesel fuel, gasoline fuel, turbine fuel, motor or lubricant oils, gearbox oils and lubricant greases.

Examples of plastics which may be stabilized by the polycyclic phenolic compounds described include:

polymers of mono- or diolefins, such as low- or high-density polyethylene, polypropylene, linear polybutene-1, polyisoprene, polybutadiene, and also copolymers of mono- or diolefins or mixtures of the polymers mentioned;

polystyrene and copolymers of styrene or α-methylstyrene with dienes and/or acrylic derivatives, for example styrene-butadiene, styrene-acrylonitrile (SAN), styrene-ethyl methacrylate, styrene-butadiene-ethyl acrylate, styrene-acrylonitrile-methacrylate, acrylonitrile-butadiene-styrene (ABS) or methyl methacrylate-butadiene-styrene (MBS); halogen-containing polymers, for example polyvinyl chloride, polyvinyl fluoride, polyvinylidene fluoride and their copolymers;

polymers which derive from α,β-unsaturated acids and their derivatives, such as polyacrylates, polymethacrylates, polyacrylamides and polyacrylonitriles;

polymers which derive from unsaturated alcohols and amines or from their acyl derivatives or acetals, for example polyvinyl alcohol and polyvinyl acetate;

polyurethanes, especially thermoplastic polyurethanes, polyamides, polyureas, polyphenylene ethers, polyesters, polycarbonates, polysulfones, polyether sulfones and polyether ketones.

The paints which can be stabilized with the polycyclic phenolic compounds described include coatings such as alkyd resin coatings, dispersion coatings, epoxy resin coatings, polyurethane coatings, acrylic resin coatings and cellulose nitrate coatings, or varnishes such as wood protection varnishes.

The polycyclic phenolic compounds described are suitable in a particularly advantageous manner as stabilizers in turbine fuels (jet fuels). This is also understood to mean their mode of action as antioxidants in the conventional sense. In particular, by virtue of their mode of action as stabilizers, they serve to improve the thermal stability of turbine fuels. Moreover, especially also by virtue of their action as stabilizers, i.e. in their property as dispersants, they prevent deposits in the fuel system and/or combustion system of turbines. Turbine fuels are used in particular for operating aviation turbines.

The present invention further provides a turbine fuel composition which comprises a turbine fuel (jet fuel) and at least one of the polycyclic phenolic compounds described.

The inventive turbine fuel composition comprises a majority of a liquid turbine fuel, which is, for example, a turbine fuel customary in civilian or military aviation. These include, for example, fuels of the designation Jet Fuel A, Jet Fuel A-1, Jet Fuel B, Jet Fuel JP-4, JP-5, JP-7, JP-8 and JP-8+100. Jet A and Jet A-1 are commercially available turbine fuel specifications based on kerosene. The accompanying standards are ASTM D 1655 and DEF STAN 91-91. Jet B is a more highly cut fuel based on naphtha and kerosene fractions. JP-4 is equivalent to Jet B. JP-5, JP-7, JP-8 and JP-8+100 are military turbine fuels, as used, for example, by the Marines and Air Force. Some of these standards relate to formulations which already comprise further additives such as corrosion inhibitors, icing inhibitors, static dissipators, etc.

The polycyclic phenolic compounds described may be added to the turbine fuel or to the turbine fuel composition individually, as mixtures and, if appropriate, in combination with further additives known per se.

Suitable additives which may be present in the inventive turbine fuel composition comprise typically detergents, corrosion inhibitors, further antioxidants such as sterically hindered tert-butylphenols, N-butylphenylenediamines or N,N'-diphenylamine and derivatives thereof, metal deactivators such as N,N'-disalicylidene-1,2-diamino-propane, solubilizers, antistats such as Stadis 450, biocides, anti-icing agents such as diethylene glycol methyl ether, and also mixtures of the additives mentioned.

Additives preferred in the context of the present invention are the specific compound classes (A), (B) and (C) detailed below:

Preferred additives (A) are compounds which derive from succinic anhydride and have long-chain hydrocarbon radicals having generally from 15 to 700, in particular from 30 to 200 carbon atoms. These compounds may have further functional groups which are preferably selected from hydroxyl, amino, amido and/or imido groups. Preferred additives are the corresponding derivatives of polyalkenylsuccinic anhydride which are obtainable, for example, by reacting polyalkenes with maleic anhydride by a thermal route or via the chlorinated hydrocarbons. The number-average molecular weight of the long-chain hydrocarbon radicals is preferably in a range from about 200 to 10 000, more preferably from 400 to 5000, in particular from 600 to 3000 and especially from 650 to 2000. These long-chain hydrocarbon radicals preferably derive from conventional polyisobutenes and especially from the aforementioned reactive polyisobutenes. Of particular interest as additives (A) are the derivatives of polyalkenylsuccinic anhydrides with ammonia, monoamines, polyamines, monoalcohols and polyols. Polyamines preferred for derivatization comprise ethylenediamine, diethylene-triamine, triethylenetetramine, tetraethylenepentamine, propylenediamine, etc. Suitable alcohols comprise monohydric alcohols such as ethanol, allyl alcohol, dodecanol and benzyl alcohol, polyhydric alcohols such as ethylene glycol, diethylene glycol, propylene glycol, 1,2-butanediol, neopentyl glycol, glycerol, trimethylolpropane, erythritol, pentaerythritol, mannitol and sorbitol.

Succinic anhydride derivatives (A) suitable as additives are described, for example, in U.S. Pat. Nos. 3,522,179, 4,234,435, 4,849,572, 4,904,401, 5,569,644 and 6,165,235, which is fully incorporated here by reference.

Preferred additives (B) are polyalkenylthiophosphonate esters. The polyalkenyl radical of these esters preferably has a number-average molecular weight in the range from about 300 to 5000, more preferably from 400 to 2000 and in particular from 500 to 1500. The polyalkenyl radical derives preferably from polyolefins as have already been described as long-chain hydrocarbon radical for component (A). They are especially polyalkenyl radicals which derive from conventional or reactive polyisobutenes. Suitable processes for preparing suitable polyalkenylthiophosphonate esters by reacting a polyolefin with a thiophosphorylating agent are described, for example, in U.S. Pat. No. 5,725,611, which is incorporated here by reference.

Preferred additives (C) are Mannich adducts. Such adducts are obtained in principle by Mannich reaction of aromatic hydroxyl compounds, especially phenol and phenol derivatives, with aldehydes and mono- or polyamines. They are preferably the reaction products of polyisobutene-substituted phenols with formaldehyde and mono- or polyamines such as ethylenediamine, diethylenetriamine, triethylenetetramine, tetraethylenepentamine, dimethylaminopropylamine, etc. Suitable Mannich adducts and processes for their preparation are described, for example, in U.S. Pat. No. 5,876,468, EP-A 831 141, EP-A 1 233 990 and EP-A 1 226 188, which are fully incorporated here by reference.

The inventive turbine fuel composition comprises the polycyclic phenolic compounds described in an amount of typically from 0.0001 to 1% by weight, preferably from 0.001 to 0.5% by weight, especially from 0.01 to 0.2% by weight and in particular from 0.01 to 0.1% by weight, based on the total amount of the turbine fuel composition.

The additives (A) to (C) and, if appropriate, further additives from those mentioned above may typically each be used in amounts of in each case from 0.0001 to 1% by weight, preferably from 0.001 to 0.6% by weight and in particular from 0.0015 to 0.4% by weight, based on the total amount of the turbine fuel composition.

The present invention further provides an additive concentrate for turbine fuels Oet fuels) which comprises at least one of the polycyclic phenolic compounds described and, if appropriate, at least one diluent and, if appropriate, at least one further additive which is preferably selected from those described above. In a preferred embodiment, the inventive additive concentrate, and hence also the inventive turbine fuel composition, comprises one or more additives from the group of (A), (B) and (C), especially also mixtures thereof such as (A)+(B), (A)+(C), (B)+(C) and (A)+(B)+(C).

Suitable diluents are, for example, fractions obtained in crude oil processing, such as kerosene, naphtha or mineral base oils. Also suitable are aromatic and aliphatic hydrocarbons such as Solvent Naphtha heavy, Solvesso® or Shellsol®, and also mixtures of these solvents and diluents.

The polycyclic phenolic compounds described are present in the inventive additive concentrate preferably in an amount of from 0.1 to 100% by weight, more preferably from 1 to 80% by weight and in particular from 10 to 70% by weight, based on the total weight of the concentrate.

The polycyclic phenolic compounds described are also advantageously suitable as stabilizers in gasoline fuels and in middle distillate fuels, here especially in diesel fuel and heating oil. This should also be understood to include their mode of action as antioxidants in the conventional sense. In particular, they serve, by virtue of their mode of action as stabilizers, to improve the thermal stability of gasoline fuels and middle distillate fuels. In particular, by virtue of their mode of action as stabilizers, i.e. in their property as dispersants, they also serve to prevent deposits in the fuel system and/or combustion system of gasoline or diesel engines.

Possible gasoline fuels include all commercial gasoline fuel compositions. A typical representative which should be mentioned here is the Eurosuper base fuel according to EN 228, which is customary on the market. Gasoline fuel compositions of the specification according to WO 00/47698 are also possible fields of use for the present invention.

Possible middle distillate fuels include all commercial diesel fuel and heating oil compositions. Diesel fuels are typically mineral oil raffinates which generally have a boiling range of from 100° C. to 400° C. These are usually distillates having a 95% point up to 360° C. or even higher. They may also be so-called "ultra low sulfur diesel" or "city diesel", characterized by a 95% point of, for example, not more than 345° C. and a sulfur content of not more than 0.005% by weight, or by a 95% point of, for example, 285° C. and a sulfur content of not more than 0.001% by weight. In addition to the diesel fuels obtainable by refining, whose main constituents are relatively long-chain paraffins, suitable diesel fuels are also those which are obtainable by coal gasification or gas liquefaction ["gas-to-liquid" (GTL) fuels]. Also suitable are mixtures of the aforementioned diesel fuels with renewable fuels such as biodiesel or bioethanol. At the present time, diesel fuels with low sulfur content are of particular interest, i.e. with a sulfur content of less than 0.05% by weight, preferably of less than 0.02% by weight, in particular of less than 0.005% by weight and especially of less than 0.001% by weight, of sulfur. Diesel fuels may also comprise water, for example in an amount up to 20% by weight, for example in the form of diesel-water microemulsions or as so-called "white diesel".

Heating oils are, for example, low-sulfur or sulfur-rich mineral oil raffinates, or bituminous coal distillates or brown coal distillates, which typically have a boiling range of from 150 to 400° C. The heating oils may be standard heating oil according to DIN 51603-1, which has a sulfur content of from 0.005 to 0.2% by weight, or be low-sulfur heating oils having a sulfur content of from 0 to 0.005% by weight. Examples of heating oil include in particular heating oil for domestic oil-fired boilers or EL heating oil.

The polycyclic phenolic compounds described can be added either to the particular base fuel, especially to the gasoline fuel or to the diesel fuel, alone or in the form of fuel additive packages, for example so-called diesel performance packages. Such packages are fuel additive concentrates and generally comprise, in addition to solvents, a series of further components as coadditives, for example carrier oils, cold flow improvers, corrosion inhibitors, demulsifiers, dehazers, antifoams, further cetane number improvers, further combustion improvers, antioxidants or stabilizers, antistats, metallocenes, metal deactivators, solubilizers, markers and/or dyes.

In a preferred embodiment, the additized gasoline fuel or diesel fuel, in addition to the polycyclic phenolic compounds described, comprises, as further fuel additives, in particular at least one detergent, referred to hereinafter as component (D).

Detergents or detergent additives typically refer to deposition inhibitors for fuels. The detergents are preferably amphiphilic substances which have at least one hydrophobic hydrocarbon radical having a number-average molecular weight ($M_n$) of from 85 to 20 000, especially from 300 to 5000 and in particular from 500 to 2500, and at least one polar moiety which is selected from (Da) mono- or polyamino groups having up to 6 nitrogen atoms, at least one nitrogen atom having basic properties;
(Db) nitro groups, if appropriate in combination with hydroxyl groups;
(Dc) hydroxyl groups in combination with mono- or polyamino groups, at least one nitrogen atom having basic properties;
(Dd) carboxyl groups or their alkali metal or alkaline earth metal salts;
(De) sulfonic acid groups or their alkali metal or alkaline earth metal salts;
(Df) polyoxy-$C_2$-$C_4$-alkylene moieties which are terminated by hydroxyl groups, mono- or polyamino groups, at least one nitrogen atom having basic properties, or by carbamate groups;
(Dg) carboxylic ester groups;
(Dh) moieties which derive from succinic anhydride and have hydroxyl and/or amino and/or amido and/or imido groups; and/or
(Di) moieties obtained by Mannich reaction of substituted phenols with aldehydes and mono- or polyamines.

The hydrophobic hydrocarbon radical in the above detergent additives, which ensures the adequate solubility in the fuel oil composition, has a number-average molecular weight ($M_n$) of from 85 to 20 000, especially from 300 to 5000, in particular from 500 to 2500. Typical hydrophobic hydrocarbon radicals, especially in conjunction with the polar moieties (Da), (Dc), (Dh) and (Di), include relatively long-chain alkyl or alkenyl groups, especially the polypropenyl, polybutenyl and polyisobutenyl radical, each having $M_n$=from 300 to 5000, especially from 500 to 2500, in particular from 700 to 2300.

Examples of the above groups of detergent additives include the following:

Additives comprising mono- or polyamino groups (Da) are preferably polyalkenemono- or polyalkenepolyamines based on polypropene or conventional (i.e. having predominantly internal double bonds) polybutene or polyisobutene having $M_n$=from 300 to 5000. When polybutene or polyisobutene having predominantly internal double bonds (usually in the β- and γ-position) are used as starting materials in the preparation of the additives, a possible preparative route is by chlorination and subsequent amination or by oxidation of the double bond with air or ozone to give the carbonyl or carboxyl compound and subsequent amination under reductive (hydrogenating) conditions. The amines used here for the amination may be, for example, ammonia, monoamines or polyamines, such as dimethylaminopropylamine, ethylenediamine, diethylenetriamine, triethylenetetramine or tetraethylenepentamine. Corresponding additives based on polypropene are described in particular in WO-A-94124231.

Further preferred additives comprising monoamino groups (Da) are the hydrogenation products of the reaction products of polyisobutenes having an average degree of polymerization P=from 5 to 100 with nitrogen oxides or mixtures of nitrogen oxides and oxygen, as described in particular in WO-A-97/03946.

Further preferred additives comprising monoamino groups (Da) are the compounds obtainable from polyisobutene epoxides by reaction with amines and subsequent dehydration and reduction of the amino alcohols, as described in particular in DE-A-196 20 262.

Additives comprising nitro groups (Db), if appropriate in combination with hydroxyl groups, are preferably reaction products of polyisobutenes having an average degree of polymerization P=from 5 to 100 or from 10 to 100 with nitrogen oxides or mixtures of nitrogen oxides and oxygen, as described in particular in WO-A-96103367 and WO-A-96/03479. These reaction products are generally mixtures of pure nitropolyisobutenes (e.g. α,β-dinitropolyisobutene) and mixed hydroxynitropolyiso-butenes (e.g. α-nitro-β-hydroxypolyisobutene).

Additives comprising hydroxyl groups in combination with mono- or polyamino groups (Dc) are in particular reaction products of polyisobutene epoxides obtainable from polyisobutene having preferably predominantly terminal double bonds and $M_n$=from 300 to 5000, with ammonia or mono- or polyamines, as described in particular in EP-A-476 485.

Additives comprising carboxyl groups or their alkali metal or alkaline earth metal salts (Dd) are preferably copolymers of $C_2$-$C_{40}$-olefins with maleic anhydride which have a total molar mass of from 500 to 20 000 and of whose carboxyl groups some or all have been converted to the alkali metal or alkaline earth metal salts and any remainder of the carboxyl groups has been reacted with alcohols or amines. Such additives are disclosed in particular by EP-A-307 815. Such additives serve mainly to prevent valve seat wear and can, as described in WO-A-87/01126, advantageously be used in combination with customary fuel detergents such as poly(iso)buteneamines or polyetheramines.

Additives comprising sulfonic acid groups or their alkali metal or alkaline earth metal salts (De) are preferably alkali metal or alkaline earth metal salts of an alkyl sulfosuccinate, as described in particular in EP-A-639 632. Such additives serve mainly to prevent valve seat wear and can be used advantageously in combination with customary fuel detergents such as poly(iso)buteneamines or polyetheramines.

Additives comprising polyoxy-$C_2$-$C_4$-alkylene moieties (Df) are preferably polyethers or polyether amines which are obtainable by reaction of $C_2$-$C_{60}$-alkanols, $C_6$-$C_{30}$-alkanediols, mono- or di-$C_2$-$C_{30}$-alkylamines, $C_1$-$C_{30}$-alkylcyclohexanols or $C_1$-$C_{30}$-alkylphenols with from 1 to 30 mol of ethylene oxide and/or propylene oxide and/or butylene oxide per hydroxyl group or amino group and, in the case of the polyether amines, by subsequent reductive amination with ammonia, monoamines or polyamines. Such products are described in particular in EP-A-310 875, EP-A-356 725, EP-A-700 985 and U.S. Pat. No. 4,877,416. In the case of polyethers, such products also have carrier oil properties. Typical examples of these are tridecanol butoxylates, isotridecanol butoxylates, isononylphenol butoxylates and polyisobutenol butoxylates and propoxylates and also the corresponding reaction products with ammonia.

Additives comprising carboxylic ester groups (Dg) are preferably esters of mono-, di- or tricarboxylic acids with long-chain alkanols or polyols, in particular those having a minimum viscosity of 2 mm$^2$/s at 100° C., as described in particular in DE-A-38 38 918. The mono-, di- or tricarboxylic acids used may be aliphatic or aromatic acids, and particularly suitable ester alcohols or ester polyols are long-chain representatives having, for example, from 6 to 24 carbon atoms. Typical representatives of the esters are adipates, phthalates, isophthalates, terephthalates and trimellitates of isooctanol, of isononanol, of isodecanol and of isotridecanol. Such products also have carrier oil properties.

Additives comprising moieties derived from succinic anhydride and having hydroxyl and/or amino and/or amido and/or imido groups (Dh) are preferably corresponding derivatives of alkyl- or alkenyl-substituted succinic anhydride and especially the corresponding derivatives of polyisobutenylsuccinic anhydride which are obtainable by reacting conventional or highly reactive polyisobutene having Mn=from 300 to 5000 with maleic anhydride by a thermal route or via the chlorinated polyisobutene.

Particular interest attaches to derivatives with aliphatic polyamines such as ethylenediamine, diethylenetriamine, triethylenetetramine or tetraethylenepentamine. The moieties having hydroxyl and/or amino and/or amido and/or imido groups are, for example, carboxylic acid groups, acid amides of monoamines, acid amides of di- or polyamines which, in addition to the amide function, also have free amine groups, succinic acid derivatives having an acid and an amide function, carboximides with monoamines, carboximides with di- or polyamines which, in addition to the imide function, also have free amine groups, or diimides which are formed by the reaction of di- or polyamines with two succinic acid derivatives. Such fuel additives are described in particular in U.S. Pat. No. 4,849,572.

The detergent additives from group (Dh) are preferably the reaction products of alkyl- or alkenyl-substituted succinic anhydrides, especially of polyisobutenylsuccinic anhydrides, with amines and/or alcohols. They are thus derivatives which are derived from alkyl-, alkenyl- or polyisobutenylsuccinic anhydride and have amino and/or amido and/or imido and/or hydroxyl groups. It will be appreciated that these reaction products are not only obtainable when substituted succinic anhydride is used, but also when substituted succinic acid or suitable acid derivatives, such as succinyl halides or succinic esters, are used.

In a preferred embodiment, the additized fuel comprises at least one detergent based on a polyisobutenyl-substituted succinimide. Of special interest are the imides with aliphatic polyamines. Particularly preferred polyamines are ethylenediamine, diethylenetriamine, triethylenetetramine, pentaethylenehexamine, and in particular tetraethylenepentamine. The polyisobutenyl radical has a number-average molecular weight $M_n$ of preferably from 500 to 5000, more preferably from 500 to 2000 and in particular of about 1000.

Additives comprising moieties (Di) obtained by Mannich reaction of substituted phenols with aldehydes and mono- or polyamines are preferably reaction products of polyisobutene-substituted phenols with formaldehyde and mono- or polyamines such as ethylenediamine, diethylenetriamine, triethylenetetramine, tetraethylenepentamine or dimethylaminopropylamine. The polyisobutenyl-substituted phenols may stem from conventional or highly reactive polyisobutene having $M_n$=from 300 to 5000. Such "polyisobutene-Mannich bases" are described in particular in EP-A-831 141.

The detergent additives (D) mentioned together with the polycyclic phenolic compounds described are preferably used in combination with at least one carrier oil.

Suitable mineral carrier oils are the fractions obtained in crude oil processing, such as brightstock or base oils having viscosities, for example, from the SN 500-2000 class; but also aromatic hydrocarbons, paraffinic hydrocarbons and alkoxyalkanols. Likewise useful is a fraction which is obtained in the refining of mineral oil and is known as "hydrocrack oil" (vacuum distillate cut having a boiling range of from about 360 to 500° C., obtainable from natural mineral oil which has been catalytically hydrogenated under high pressure and isomerized and also deparaffinized). Likewise suitable are mixtures of abovementioned mineral carrier oils.

Examples of suitable synthetic carrier oils are selected from: polyolefins (poly-alpha-olefins or poly(internal olefin)s), (poly)esters, (poly)alkoxylates, polyethers, aliphatic polyether amines, alkylphenol-started polyethers, alkylphenol-started polyether amines and carboxylic esters of long-chain alkanols.

Examples of suitable polyolefins are olefin polymers having $M_n$=from 400 to 1800, in particular based on polybutene or polyisobutene (hydrogenated or unhydrogenated).

Examples of suitable polyethers or polyetheramines are preferably compounds comprising polyoxy-$C_2$-$C_4$-alkylene moieties which are obtainable by reacting $C_2$-$C_{60}$-alkanols, $C_6$-$C_{30}$-alkanediols, mono- or di-$C_2$-$C_{30}$-alkylamines, $C_1$-$C_{30}$-alkylcyclo-hexanols or $C_1$-$C_{30}$-alkylphenols with from 1 to 30 mol of ethylene oxide and/or propylene oxide and/or butylene oxide per hydroxyl group or amino group, and, in the case of the polyether amines, by subsequent reductive amination with ammonia, monoamines or polyamines. Such products are described in particular in EP-A-310 875, EP-A-356 725, EP-A-700 985 and U.S. Pat. No. 4,877,416. For example, the polyether amines used may be poly-$C_2$-$C_6$-alkylene oxide amines or functional derivatives thereof. Typical examples thereof are tridecanol butoxylates or isotridecanol butoxylates, isononylphenol butoxylates and also polyisobutenol butoxylates and propoxylates, and also the corresponding reaction products with ammonia.

Examples of carboxylic esters of long-chain alkanols are in particular esters of mono-, di- or tricarboxylic acids with long-chain alkanols or polyols, as described in particular in DE-A-38 38 918. The mono-, di- or tricarboxylic acids used may be aliphatic or aromatic acids; suitable ester alcohols or polyols are in particular long-chain representatives having, for example, from 6 to 24 carbon atoms. Typical representatives of the esters are adipates, phthalates, isophthalates, terephthalates and trimellitates of isooctanol, isononanol, isodecanol and isotridecanol, for example di-(n- or isotridecyl)phthalate.

Further suitable carrier oil systems are described, for example, in DE-A-38 26 608, DE-A-41 42 241, DE-A-43 09 074, EP-A-0 452 328 and EP-A-0 548 617.

Examples of particularly suitable synthetic carrier oils are alcohol-started polyethers having from about 5 to 35, for example from about 5 to 30, $C_3$-$C_6$-alkylene oxide units, for example selected from propylene oxide, n-butylene oxide and isobutylene oxide units, or mixtures thereof. Nonlimiting examples of suitable starter alcohols are long-chain alkanols or phenols substituted by long-chain alkyl in which the long-chain alkyl radical is in particular a straight-chain or branched $C_6$-$C_{18}$-alkyl radical. Preferred examples include tridecanol and nonylphenol.

Further suitable synthetic carrier oils are alkoxylated alkylphenols, as described in DE-A-10 102 913.

Preferred carrier oils are synthetic carrier oils, particular preference being given to polyethers.

The detergent additive (D) or a mixture of different detergent additives of this type is added to the additized fuel in a total amount of preferably from 10 to 2000 ppm by weight, more preferably from 20 to 1000 ppm by weight, even more preferably from 50 to 500 ppm by weight and in particular from 50 to 200 ppm by weight, for example from 70 to 150 ppm by weight.

When a carrier oil is used additionally, it is added to the inventive additized fuel in an amount of preferably from 1 to 1000 ppm by weight, more preferably from 10 to 500 ppm by weight and in particular from 20 to 100 ppm by weight.

Cold flow improvers suitable as further coadditives are, for example, copolymers of ethylene with at least one further unsaturated monomer, for example ethylene-vinyl acetate copolymers.

Corrosion inhibitors suitable as further coadditives are, for example, succinic esters, in particular with polyols, fatty acid derivatives, for example oleic esters, oligomerized fatty acids and substituted ethanolamines.

Demulsifiers suitable as further coadditives are, for example, the alkali metal and alkaline earth metal salts of alkyl-substituted phenolsulfonates and naphthalene-sulfonates, and the alkali metal and alkaline earth metal salts of fatty acid, and also alcohol alkoxylates, e.g. alcohol ethoxylates, phenol alkoxylates, e.g. tert-butylphenol ethoxylates or tert-pentylphenol ethoxylates, fatty acid, alkylphenols, condensation products of ethylene oxide and propylene oxide, e.g. ethylene oxide-propylene oxide block copolymers, polyethyleneimines and polysiloxanes.

Dehazers suitable as further coadditives are, for example, alkoxylated phenol-formaldehyde condensates.

Antifoams suitable as further coadditives are, for example, polyether-modified polysiloxanes.

Cetane number improvers and combustion improvers suitable as further coadditives are, for example, alkyl nitrates, e.g. cyclohexyl nitrate and especially 2-ethylhexyl nitrate, and peroxides, e.g. di-tert-butyl peroxide.

Antioxidants suitable as further coadditives are, for example, substituted phenols, e.g. 2,6-di-tert-butylphenol and 2,6-di-tert-butyl-3-methylphenol, and phenylenediamines, e.g. N,N'-di-sec-butyl-p-phenylenediamine.

Metal deactivators suitable as further coadditives are, for example, salicylic acid derivatives, e.g. N,N'-disalicylidene-1,2-propanediamine.

Suitable solvents, especially for fuel additive packages, are, for example, nonpolar organic solvents, especially aromatic and aliphatic hydrocarbons, for example toluene, xylenes, "white spirit" and the technical solvent mixtures with the names Shellsol® (manufacturer: Royal Dutch/Shell Group), Exxol® (manufacturer: ExxonMobil) and Solvent Naphtha. Also useful here, especially in a blend with the nonpolar organic solvents mentioned, are polar organic solvents, in particular alcohols such as 2-ethylhexanol, decanol and isotridecanol.

When the coadditives and/or solvents mentioned are also used in gasoline fuel or diesel fuel, they are used in the amounts customary therefor.

The polycyclic phenolic compounds described are also suitable particularly advantageously as stabilizers in lubricants. Lubricants or lubricant compositions shall be understood here to mean motor oils, lubricant oils, transmission oils including manual and automatic oils, and related fluid compositions which serve to lubricate mechanically moving parts—usually as the metal. Stabilization is understood here to mean in particular the improvement in the oxidation and aging stability of lubricant compositions, i.e. their action as antioxidants in particular. In addition or alternatively, the polycyclic phenolic compounds described improve the shear stability of lubricant compositions, i.e. the polycyclic phenolic compounds thicken the lubricant compositions more effectively. In some cases, the polycyclic phenolic compounds described also act as dispersants in lubricant compositions.

The present invention further provides a lubricant composition which comprises components customary therefor and at least one of the polycyclic phenolic compounds described. The inventive lubricant composition comprises the polycyclic phenolic compounds described in an amount of typically from 0.001 to 20% by weight, preferably from 0.01 to 10% by weight, especially from 0.05 to 8% by weight and in particular from 0.1 to 5% by weight, based on the total amount of the lubricant composition.

The economically most significant lubricant compositions are motor oils, and also transmission oils including manual and automatic oils. Motor oils consist typically of mineral base oils which comprise predominantly paraffinic constituents and are produced in the refinery by costly inconvenient workup and purification processes, having a fraction of from approx. 2 to 10% by weight of additives (based on the active substance contents). For specific applications, for example high-temperature applications, the mineral base oils may be replaced partly or fully by synthetic components such as organic esters, synthetic hydrocarbons such as olefin oligomers, poly-α-olefins or polyolefins of hydrocracking oils. Motor oils also have to have sufficiently high viscosities at high temperatures in order to ensure impeccable lubrication effect and good sealing between cylinder and piston. Moreover, the flow properties of motor oils have to be such that the engine can be started without any problem at low temperatures. Motor oils have to be oxidation-stable and must generate only small amounts of decomposition products in liquid or solid form and deposits even under difficult working conditions. Motor oils disperse solids (dispersant behavior), prevent deposits (detergent behavior), neutralize acidic reaction products and form a protective film on the metal surfaces in the engine. Motor oils are typically characterized by viscosity classes (SAE classes).

With regard to their base components and additives, transmission oils including manual and automatic oils have a similar composition to motor oils. The force is transmitted in the gear system of gearboxes to a high degree through the liquid pressure in the transmission oil between the teeth. The transmission oil accordingly has to be such that it withstands high pressures for prolonged periods without decomposing. In addition to the viscosity properties, wear, pressure resistance, friction, shear stability, traction and running-in performance are the crucial parameters here.

In addition to the polycyclic phenolic compounds to be used in the context of the present invention, motor oils and transmission oils including manual and automatic oils generally also comprise at least one, but usually some or all, of the additives listed below in the amounts customary therefor (which are stated in brackets in % by weight, based on the overall lubricant composition):

(a) antioxidants (from 0.1 to 5%):
   sulfur compounds, for example reaction products of terpenes (α-pinene), resin oils or low molecular weight polybutenes with sulfur, dialkyl sulfides, dialkyl trisulfides, polysulfides, diaryl sulfides, modified thiols, mercaptobenzimidazoles, mercaptotriazines, thiophene derivatives, xanthates, zinc dialkyldithiocarbamates, thioglycols, thioaldehydes, dibenzyl disulfide, alkylphenol sulfides, dialkylphenol sulfides or sulfur-containing carboxylic acids phosphorus compounds, for example triaryl and trialkyl phosphites, dialkyl 3,5-di-tert-butyl-4-hydroxybenzylphosphonate or phosphonic acid piperazides
   sulfur-phosphorus compounds, for example zinc dialkyldithiophosphates (metal dialkyldithiophosphates also act as corrosion inhibitors and high-pressure additives in lubricant oils) or reaction products of phosphorus pentasulfide with terpenes (α-pinene, dipentene), polybutenes, olefins or unsaturated esters
   phenol derivatives, for example sterically hindered mono-, bis- or trisphenols, sterically hindered polycyclic phenols, polyalkylphenols, 2,6-di-tert-butyl-4-methylphenol or methylene-4,4'-bis(2,6-di-tert-butylphenol) (phenol derivatives are often used in combination with sulfur-based or amine-based antioxidants)
   amines, for example arylamines such as diphenylamine, phenyl-α-naphthylamine or 4,4'-tetramethyldiaminodiphenylmethane
metal deactivators in the narrower sense, for example N-salicylideneethylamine, N,N'-disalicylideneethylenediamine, N,N'-disalicylidene-1,2-propanediamine, triethylenediamine, ethylenediaminetetraacetic acid, phosphoric acid, citric acid, glycolic acid, lecithin, thiadiazole, imidazole or pyrazole derivatives (b) viscosity index improvers (from 0.05 to 10%), for example: polyisobutenes having a molecular weight of typically from 10 000 to 45 000, polymethacrylates having a molecular weight of typically from 15 000 to 100 000, homo- and copolymers of 1,3-dienes such as butadiene or isoprene having a molecular weight of typically from 80 000 to 100 000, 1,3-diene-styrene copolymers having a molecular weight of typically from 80 000 to 100 000, maleic anhydride-styrene polymers in esterified form having a molecular weight of typically from 60 000 to 120 000, star-shaped polymers with block-like structure by virtue of units composed of conjugated dienes and aromatic monomers having a molecular weight of typically from 200 000 to 500 000, polyalkylstyrenes having a molecular weight of typically from 80 000 to 150 000, polyolefins composed of ethylene and propylene or styrene-cyclopentadiene-norbornene terpolymers having a molecular weight of typically from 60 000 to 140 000

(c) pour point depressants (cold flow improvers) (from 0.03 to 1%), for example bicyclic aromatics such as naphthalene with different long-chain alkyl radicals, polymethacrylates with from 12 to 18 carbon atoms in the alcohol radical, a degree of branching between 10 to 30 mol % and an average molecular weight of from 5000 to 500 000, long-chain alkylphenols and dialkylaryl phthalates or copolymers of different olefins (d) detergents (HD additives) (from 0.2 to 4%), for example calcium naphthenates, lead naphthenates, zinc naphthenates and manganese naphthenates, calcium dichlorostearates, calcium phenylstearates, calcium chlorophenylstearates, sulfonation products of alkylaromatics such as dodecylbenzene, petroleum sulfonates, sodium sulfonates, calcium sulfonates, barium sulfonates or magnesium sulfonates, neutral, basic and overbased sulfonates, phenates and carboxylates, salicylates, metal salts of alkylphenols and alkylphenol sulfides, phosphates, thiophosphates or alkenylphosphonic acid derivatives (e) ashless dispersants (from 0.5 to 10%), for example Mannich condensates of alkylphenol, formaldehyde and polyalkylenepolyamines, reaction products of polyisobutenylsuccinic anhydrides with polyhydroxyl compounds or polyamines, copolymers of alkyl methacrylates with diethylaminoethyl methacrylate, N-vinylpyrrolidone, N-vinylpyridine or 2-hydroxyethyl methacrylate or vinyl acetate-fumarate copolymers (f) high-pressure additives (extreme pressure additives) (from 0.2 to 2.5%), for example chlorinated paraffins with chlorine content from 40 to 70% by weight, chlorinated fatty acid (especially having trichloromethyl end groups), dialkyl hydrogenphosphites, triaryl phosphites, aryl phosphates such as tricresyl phosphate, dialkyl phosphates, trialkyl phosphates such as tributyl phosphate, trialkylphosphines, diphosphoric esters, nitroaromatics, aminophenol derivatives of naphthenic acid, carbamic esters, dithiocarbamic acid derivatives, substituted 1,2,3-triazoles, mixtures of benzotriazole and alkylsuccinic anhydride or alkylmaleic anhydride, 1,2,4-thiadiazole polymers, morpholinobenzothiadiazole disulfide, chlorinated alkyl sulfides, sulfurized olefins, sulfurized chloronaphthalenes, chlorinated alkyl thiocarbonates, organic sulfides and polysulfides such as bis(4-chlorobenzyl) disulfide and tetrachlorodiphenyl sulfide, trichloroacrolein mercaptals or especially zinc dialkyldithiophosphates (ZDDPs)

(g) friction modifiers (from 0.05 to 1%), especially polar oil-soluble compounds which generate a thin layer on the frictional surface by adsorption, for example fatty alcohols, fatty amides, fatty acid salts, fatty acid alkyl esters or fatty acid glycerides (h) antifoam additives (from 0.0001 to 0.2%), for example liquid silicones such as polydimethylsiloxanes or polyethylene glycol ethers and sulfides (i) demulsifiers (from 0.1 to 1%), for example dinonyinaphthalenesulfonates in the form of their alkali metal and alkaline earth metal salts (j) corrosion inhibitors (also known as metal deactivators) (from 0.01 to 2%), for example tertiary amines and salts thereof, imino esters, amide oximes, diaminomethanes, derivatives of saturated or unsaturated fatty acids with alkanolamines, alkylamines, sarcosines, imidazolines, alkylbenzotriazoles, dimercaptothiadiazole derivatives, diaryl phosphates, thiophosphoric esters, neutral salts of primary n-$C_8$-$C_{18}$-alkylamines or cycloalkylamines with dialkyl phosphates having branched $C_5$-$C_{12}$-alkyl groups, neutral or basic alkaline earth metal sulfonates, zinc naphthenates, mono- and dialkylaryl sulfonates, barium dinonyinaphthalenesulfonates, lanolin (wool fat), heavy metal salts of naphthenic acid, dicarboxylic acid, unsaturated fatty acids, hydroxy fatty acids, fatty acid esters, pentaerythrityl monooleates and sorbitan monooleates, O-stearoylalkanolamines, polyisobutenylsuccinic acid derivatives or zinc dialkyldithiophosphates and zinc dialkyldithiocarbamates (k) emulsifiers (from 0.01 to 1%), for example long-chain unsaturated, naturally occurring carboxylic acid, naphthenic acids, synthetic carboxylic acid, sulfonamides, N-oleylsarcosine, alkanesulfamidoacetic acid, dodecylbenzenesulfonate, long-chain alkylated ammonium salts such as dimethyldodecylbenzylammonium chloride, imidazolinium salts, alkyl-, alkylaryl-, acyl-, alkylamino- and acylaminopolyglycols or long-chain acylated mono- and diethanolamines (l) dyes and fluorescence additives (from 0.001 to 0.2%)

(m) preservatives (from 0.001 to 0.5%)

(n) odor improvers (from 0.001 to 0.2%).

Typical ready-to-use motor oil formulations and transmission oil, including manual and automatic oil, formulations in the context of the present invention have the following composition, the data for the additives relating to the active substance contents and the sum of all components always adding up to 100% by weight:

from 80 to 99.3% by weight, in particular from 90 to 98% by weight of motor oil base or transmission oil, including manual and automatic oil, base (mineral base oils and/or synthetic components) including the fractions of solvent and diluent for the additives from 0.1 to 8% by weight of polycyclic phenol compounds as stabilizers from 0.2 to 4% by weight, in particular from 1.3 to 2.5% by weight of detergents of group (d)

from 0.5 to 10% by weight, in particular from 1.3 to 6.5% by weight of dispersants of group (e)

from 0.1 to 5% by weight, in particular from 0.4 to 2.0% by weight of antioxidants of group (a) and/or high-pressure additives of group (f) and/or friction modifiers of group (g)

from 0.05 to 10% by weight, in particular from 0.2 to 1.0% by weight of viscosity index improvers of group (b)

from 0 to 2% by weight of other additives of groups (c) and (h) to (n).

The present invention also provides a process for preparing the polycyclic phenolic compounds described, which comprises reacting the tetrahydrobenzoxazine I with one or more of the same or different phenols II and/or with one or more of the same or different tetrahydrobenzoxazines I at temperatures of from 60 to 250° C., in particular from 90 to 150° C., in the absence or in the presence of an inert solvent, for example an aromatic hydrocarbon such as toluene or xylene.

Since some of the polycyclic phenolic compounds described are novel substances, these novel substances themselves also form part of the subject matter of the present invention.

Polycyclic phenolic compounds having at least one relatively long-chain hydrocarbyl radical having at least 26 carbon atoms are novel. The present invention therefore also provides polycyclic phenolic compounds which have up to 20 benzene rings per molecule and are obtainable by reacting a tetrahydrobenzoxazine of the general formula I

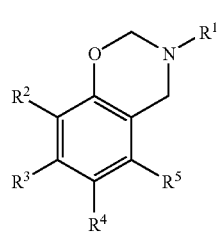

(I)

in which the substituent $R^1$ is a hydrocarbyl radical which has from 1 to 3000 carbon atoms and may be interrupted by one or more heteroatoms from the group of O and S and/or by one or more $NR^6$ moieties, where $R^6$ is a hydrogen atom or a $C_1$- to $C_4$-alkyl radical, and in which the substituents $R^2$, $R^3$, $R^4$ and $R^5$ are each independently hydrogen atoms, hydroxyl groups or hydrocarbyl radicals which have in each case from 1 to 3000 carbon atoms and may be interrupted by one or more heteroatoms from the group of O and S and/or by one or more $NR^6$ moieties, where $R^6$ is as defined above, with one or more of the same or different phenols of the general formula II

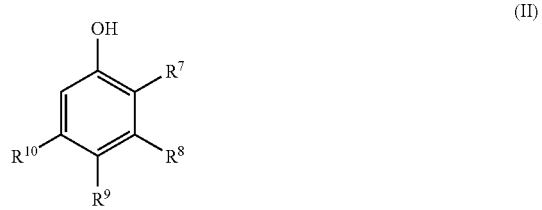

(II)

in which the substituents $R^7$, $R^8$, $R^9$ and $R^{10}$ are each independently hydrogen atoms, hydroxyl groups or hydrocarbyl radicals which have in each case from 1 to 3000 carbon atoms and may be interrupted by one or more heteroatoms from the group of O and S and/or by one or more $NR^6$ moieties, where $R^6$ is as defined above, and/or with one or more of the same or different tetrahydrobenzoxazines of the general formula I, where the substituent $R^4$ may also be a radical of the formula Z and the substituent $R^9$ may also be a radical of the formula Z'

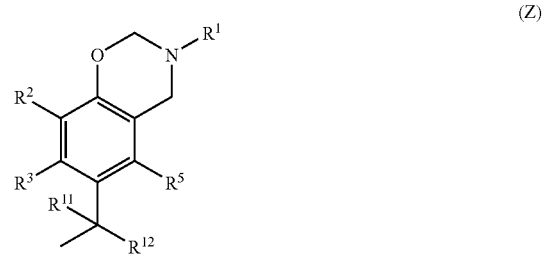

(Z)

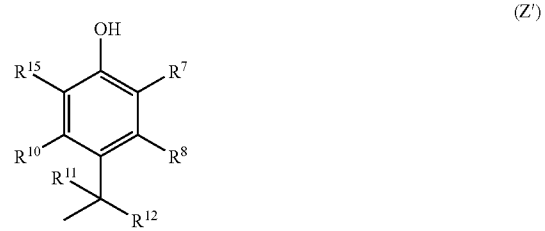

(Z')

in which the substituents $R^1$, $R^2$, $R^3$, $R^5$, $R^7$, $R^8$ and $R^{10}$ are each as defined above, the substituent $R^7$ may also be a radical derived from a tetrahydrobenzoxazine of the general formula I, the substituent $R^{15}$ is hydrogen or a radical derived from a tetrahydrobenzoxazine of the general formula I, and the substituents $R^{11}$ and $R^{12}$ may be the same or different and are each hydrogen or a $C_1$- to $C_{10}$-alkyl radical, and in which the substituents $R^2$ and $R^3$ or $R^3$ and $R^4$ or $R^4$ and $R^5$, together with the substructure —O—CH$_2$—NR$^{13}$—CH$_2$— attached to the benzene ring, may also form a second tetrahydrooxazine ring, or the substituents $R^2$ and $R^3$ and $R^4$ and $R^5$, together with the substructures —O—CH$_2$—NR$^{13}$—CH$_2$— and —O—CH$_2$—NR$^{14}$—CH$_2$— attached to the benzene ring, may also form a second and a third tetrahydrooxazine ring, where $R^{13}$ and $R^{14}$ are each independently hydrocarbyl radicals which have in each case from 1 to 3000 carbon atoms and may be interrupted by one or more heteroatoms from the group of O and S and/or by one or more $NR^6$ moieties, where $R^6$ is as defined above, with the proviso that at least one of the substituents $R^1$, $R^2$, $R^3$, $R^4$, $R^5$, $R^7$, $R^8$, $R^9$, $R^{10}$, $R^{13}$ or $R^{14}$ has from 26 to 3000 carbon atoms, and the remaining substituents from the group of $R^1$, $R^2$, $R^3$, $R^4$, $R^5$, $R^7$, $R^8$, $R^9$, $R^{10}$, $R^{13}$ or $R^{14}$, when they are hydrocarbyl radicals, each have from 1 to 20 carbon atoms.

Polycyclic phenolic compounds having at least one relatively long-chain hydrocarbyl radical having an average of at least 13 carbon atoms, which derives from oligomers or polymers of $C_2$- to $C_{12}$-olefines, are novel. The present invention therefore also provides polycyclic phenolic compounds which have up to 20 benzene rings per molecule and are obtainable by reacting a tetrahydrobenzoxazine of the general formula I

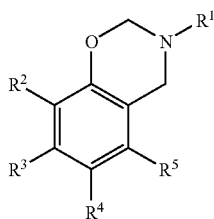

(I)

in which the substituent $R^1$ is a hydrocarbyl radical which has from 1 to 3000 carbon atoms and may be interrupted by one or more heteroatoms from the group of O and S and/or by one or more $NR^6$ moieties, where $R^6$ is a hydrogen atom or a $C_1$- to $C_4$-alkyl radical, and in which the substituents $R^2$, $R^3$, $R^4$ and $R^5$ are each independently hydrogen atoms, hydroxyl groups or hydrocarbyl radicals which have in each case from 1 to 3000 carbon atoms and may be interrupted by one or more heteroatoms from the group of O and S and/or by one or more $NR^6$ moieties, where $R^6$ is as defined above, with one or more of the same or different phenols of the general formula II

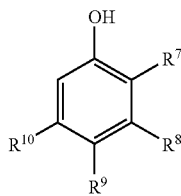

(II)

in which the substituents $R^7$, $R^8$, $R^9$ and $R^{10}$ are each independently hydrogen atoms, hydroxyl groups or hydrocarbyl radicals which have in each case from 1 to 3000 carbon atoms and may be interrupted by one or more heteroatoms from the group of O and S and/or by one or more $NR^6$ moieties, where $R^6$ is as defined above, and/or with one or more of the same or different tetrahydrobenzoxazines of the general formula I, where the substituent $R^4$ may also be a radical of the formula Z and the substituent $R^9$ may also be a radical of the formula Z'

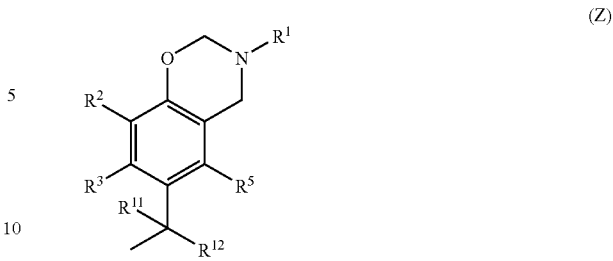

(Z)

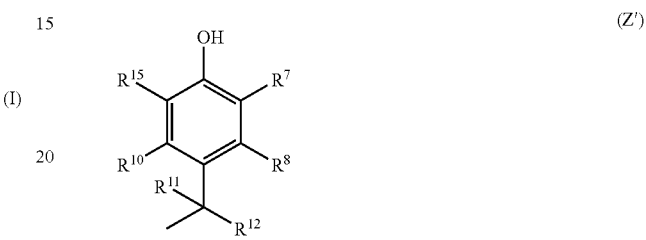

(Z')

in which the substituents $R^1$, $R^2$, $R^3$, $R^5$, $R^7$, $R^8$ and $R^{10}$ are each as defined above, the substituent $R^7$ may also be a radical derived from a tetrahydrobenzoxazine of the general formula I, the substituent $R^{15}$ is hydrogen or a radical derived from a tetrahydrobenzoxazine of the general formula I, and the substituents $R^{11}$ and $R^{12}$ may be the same or different and are each hydrogen or a $C_1$- to $C_{10}$-alkyl radical, and in which the substituents $R^2$ and $R^3$ or $R^3$ and $R^4$ or $R^4$ and $R^5$, together with the substructure —O—$CH_2$—$NR^{13}$—$CH_2$— attached to the benzene ring, may also form a second tetrahydrooxazine ring, or the substituents $R^2$ and $R^3$ and $R^4$ and $R^5$, together with the substructures —O—$CH_2$—$NR^{13}$—$CH_2$— and —O—$CH_2$—$NR^{14}$—$CH_2$— attached to the benzene ring, may also form a second and a third tetrahydrooxazine ring, where $R^{13}$ and $R^{14}$ are each independently hydrocarbyl radicals which have in each case from 1 to 3000 carbon atoms and may be interrupted by one or more heteroatoms from the group of O and S and/or by one or more $NR^6$ moieties, where $R^6$ is as defined above, with the proviso that at least one of the substituents $R^1$, $R^2$, $R^3$, $R^4$, $R^5$, $R^7$, $R^8$, $R^9$, $R^{10}$, $R^{13}$ or $R^{14}$ has on average from 13 to 3000 carbon atoms and derives from oligomers or polymers of $C_2$- to $C_{12}$-olefins, and the remaining substituents from the group of $R^1$, $R^2$, $R^3$, $R^4$, $R^5$, $R^7$, $R^8$, $R^9$, $R^{10}$, $R^{13}$ or $R^{14}$, when they are hydrocarbyl radicals, have in each case from 1 to 20 carbon atoms.

Such usually polydisperse hydrocarbyl radicals with polymeric distribution, which have on average from 13 to 3000 carbon atoms and derive from oligomers or polymers of $C_2$- to $C_{12}$-olefins, are, for example, those which derive from ethylene, propylene, butene, isobutene, styrene, methylstyrene, hexene-1, octene-1, decene-1 or dodecene-1. They may be homo- or copolymer radicals. Their number-average molecular weight $M_n$ is at least 183, their polydispersity index PDI typically from 1.05 to 10. In the case of low molecular weight radicals with $M_n$ of from 183 to approx. 500, they may also be present in monodisperse form. Of particular interest are polydisperse hydrocarbyl radicals with polymeric distribution, which derive from isobutene.

The present invention further provides oligo- and polytetrahydrobenzoxazines of the general formula III

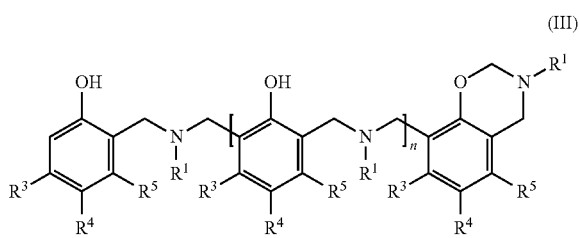

(III)

in which the substituent $R^1$ is a hydrocarbyl radical which has from 1 to 3000 carbon atoms and may be interrupted by one or more heteroatoms from the group of O and S and/or may be interrupted by one or more $NR^6$ moieties, where $R^6$ is a hydrogen atom or a $C_1$- to $C_4$-alkyl radical, in which the substituents $R^2$, $R^3$, $R^4$ and $R^5$ are each independently hydrogen atoms or hydrocarbyl radicals which have in each case from 1 to 3000 carbon atoms and may be interrupted by one or more heteroatoms from the group of O and S and/or by one or more $NR^{16}$ moieties, where $R^6$ is as defined above, and in which n is an integer from 0 to 18, with the proviso that at least one of the substituents $R^1$, $R^3$, $R^4$ or $R^5$ has from 13 to 3000 carbon atoms and the remaining substituents from the group of $R^1$, $R^3$, $R^4$ or $R^5$, when they are hydrocarbyl radicals, have in each case from 1 to 20 carbon atoms.

The present invention further provides bicyclic phenolic compounds of the general formula IV

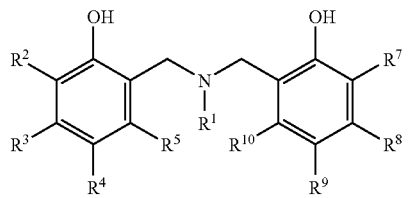

(IV)

in which the substituent $R^1$ is a hydrocarbyl radical which has from 1 to 3000 carbon atoms and may be interrupted by one or more heteroatoms from the group of O and S and/or may be interrupted by one or more $NR^6$ moieties, where $R^6$ is a hydrogen atom or a $C_1$- to $C_4$-alkyl radical, in which the substituents $R^2$, $R^3$, $R^4$, $R^5$, $R^7$, $R^8$, $R^9$ and $R^{10}$ are each independently hydrogen atoms or hydrocarbyl radicals which have in each case from 1 to 3000 carbon atoms and may be interrupted by one or more heteroatoms from the group of O and S and/or by one or more $NR^6$ moieties, where $R^6$ is as defined above, with the proviso that at least one of the substituents $R^1$, $R^2$, $R^3$, $R^4$, $R^5$, $R^7$, $R^5$, $R^9$ and $R^{10}$ has from 13 to 3000 carbon atoms and the remaining substituents from the group of $R^1$, $R^2$, $R^3$, $R^4$, $R^5$, $R^7$, $R^8$, $R^9$ and $R^{10}$, when they are hydrocarbyl radicals, have in each case from 1 to 20 carbon atoms.

The present invention further provides tricyclic phenolic compounds of the general formula V

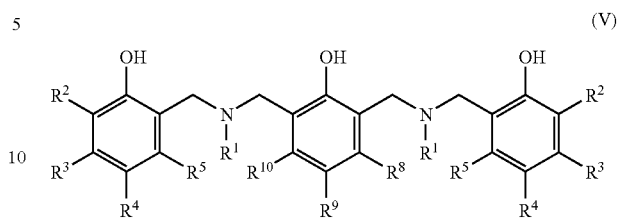

(V)

in which the substituent $R^1$ is a hydrocarbyl radical which has from 1 to 3000 carbon atoms and may be interrupted by one or more heteroatoms from the group of O and S and/or may be interrupted by one or more $NR^6$ moieties, where $R^6$ is a hydrogen atom or a $C_1$- to $C_4$-alkyl radical, in which the substituents $R^2$, $R^3$, $R^4$, $R^5$, $R^8$, $R^9$ and $R^{10}$ are each independently hydrogen atoms or hydrocarbyl radicals which have in each case from 1 to 3000 carbon atoms and may be interrupted by one or more heteroatoms from the group of O and S and/or by one or more $NR^6$ moieties, where $R^6$ is as defined above, where the substituent $R^9$ may also be a radical of the formula Z'

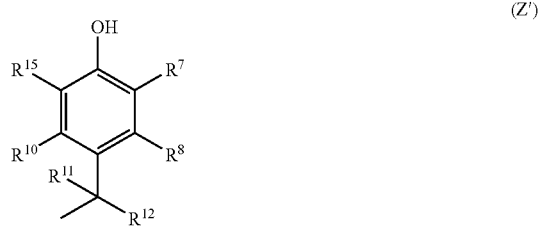

(Z')

in which the substituents $R^7$, $R^8$ and $R^{10}$ are each as defined above, the substituent $R^7$ may also be a radical derived from a tetrahydrobenzoxazine of the general formula I, the substituent $R^{15}$ is hydrogen or a radical derived from a tetrahydrobenzoxazine of the general formula I, and the substituents $R^{11}$ and $R^{12}$ may be the same or different and are each hydrogen or a $C_1$- to $C_{10}$-alkyl radical, and with the proviso that at least one of the substituents $R^1$, $R^2$, $R^3$, $R^4$, $R^1$, $R^8$, $R^9$ and $R^{10}$ has from 13 to 3000, preferably from 26 to 3000, carbon atoms, and the remaining substituents from the group of $R^1$, $R^2$, $R^3$, $R^4$, $R^5$, $R^8$, $R^9$ and $R^{10}$, when they are hydrocarbyl radicals, each have from 1 to 20 carbon atoms.

The invention will be illustrated in detail with reference to the nonlimiting examples which follow.

PREPARATION EXAMPLES

Example 1

Compound of the formula Vb by reacting
4-polyisobutenylphenol with
3-methyl-6,8-di-tert-butyltetrahydrobenzoxazine A 500 ml four-neck flask was initially charged with 120 g of 4-polyisobutenylphenol (based on the commercially available high-reactivity polyisobutene Glissopal® 1000 with an $M_n$ of 1000) at room temperature in 100 ml of toluene. 52 g of 3-methyl-6,8-di-tert-butyltetrahydrobenzoxazine were added rapidly. The flask contents were heated to reflux and stirred under reflux for 2 hours. After cooling to room temperature, the flask contents were washed with methanol and the toluene phase was concentrated by evaporation at 150° C. and 5 mbar. 113 g of product were obtained in the form of a light, clear, viscous oil.

1H NMR (400 MHz, 16 scans, $CDCl_3$):

The tetrahydrobenzoxazine signals ($\delta$=4.70 ppm, 2H, —$CH_2$—N(—$CH_3$)—$CH_2$—O—; $\delta$=3.82 ppm, 2H, —$CH_2$—N(—$CH_3$)—$CH_2$—O—) and the signal for one ortho proton of the 4-polyisobutenylphenol ($\delta$=6.70 ppm) have disappeared completely; the benzyl protons are present in the range of o=3.8-3.5 ppm, the protons of the N-methyl group in the range of $\delta$=2.6-2.0 ppm and the aromatic protons in the range of $\delta$=6.9-7.2 ppm.

Example 2

Compound of the formula Ve by reacting 4-polyisobutenylphenol with 3-(dimethylamino)propyl-6,8-di-tert-butyltetrahydrobenzoxazine A 1000 ml four-neck flask was initially charged with 170 g of 4-polyisobutenylphenol (based on the commercially available high-reactivity polyisobutene Glissopal® 1000 with an $M_n$ of 1000) at room temperature in 100 ml of toluene. 100 g of 3-(dimethylamino)propyl-6,8-di-tert-butyltetrahydrobenzoxazine were added rapidly. The flask contents were heated to reflux and stirred under reflux for 2 hours. After cooling to room temperature, the flask contents were washed with methanol and the toluene phase was concentrated by evaporation at 90° C. and 5 mbar. 225 g of product were obtained in the form of a light, clear, viscous oil.

1H NMR (400 MHz, 16 scans, $CDCl_3$):

5-10% residual tetrahydrobenzoxazine signals ($\delta$=4.70 ppm, 2H, —$CH_2$—N(—$CH_3$)—$CH_2$—O—; $\delta$=3.82 ppm, 2H, —$CH_2$—N(—$CH_3$)—$CH_2$—O—) and a small residual signal for one ortho proton of the 4-polyisobutenylphenol ($\delta$=6.70 ppm) show from 90 to 95% conversion; the benzyl protons are present in the range of $\delta$=3.8-3.4 ppm, the protons of the N-methyl and N-methylene groups in the range of $\delta$=2.6-2.0 ppm and the aromatic protons in the range of $\delta$=7.0-7.3 ppm.

Example 3

Compound of the formula Vc by reacting 4-polyisobutenylphenol with 3,6-dimethyl-8-tert-butyltetrahydrobenzoxazine A 1000 ml four-neck flask was initially charged with 240 g of 4-polyisobutenylphenol (based on the commercially available high-reactivity polyisobutene Glissopal® 1000 with an $M_n$ of 1000) at room temperature in 200 ml of toluene. 88 g of 3,6-dimethyl-8-tert-butyltetrahydrobenzoxazine were added rapidly. The flask contents were heated to reflux and stirred under reflux for 2 hours. The toluene phase was concentrated by evaporation at 150° C. and 5 mbar. 313 g of product were obtained in the form of a light, clear, viscous oil.

1H NMR (400 MHz, 16 scans, $CDCl_3$):

Residual tetrahydrobenzoxazine signals ($\delta$=4.70 ppm, 2H, —$CH_2$—N(—$CH_3$)—$CH_2$—O—; $\delta$=3.82 ppm, 2H, —$CH_2$—N(—$CH_3$)—$CH_2$—O—) and a small residual signal for one ortho proton of the 4-polyisobutenylphenol ($\delta$=6.70 ppm) show 80% conversion; the benzyl protons are present in the range of $\delta$=3.8-3.4 ppm, the protons of the N-methyl group in the range of $\delta$=2.6-2.0 ppm and the aromatic protons in the range of $\delta$=7.0-7.3 ppm.

Example 4

Compound of the formula IIIv by reacting 3-methyl-6-polyisobutenyl-tetrahydrobenzoxazine with 3-methyl-6-tert-butyltetrahydrobenzoxazine A 500 ml evaporator bulb was initially charged with 100 g of 3-methyl-6-polyisobutenyltetrahydrobenzoxazine (based on the commercially available high-reactivity polyisobutene Glissopal® 1000 with an $M_n$ of 1000) at room temperature in 200 ml of toluene. 16.4 g of 3-methyl-6-tert-butyltetrahydrobenzoxazine were added rapidly. The toluene was distilled off on a rotary evaporator at 100° C./5 mbar and the mixture was stirred at 160° C./900 mbar for 4 hours. 110 g of product were obtained in the form of a viscous oil.

1H NMR (400 MHz, 16 scans, $CDCl_3$):

Based on the integral of the methyl protons (benzoxazine: 2.45-2.65 ppm; 2-hydroxy-benzylamine: 2.05-2.30 ppm), two phenol units are joined to one benzoxazine.

Example 5

Compound of the formula IIIw by reacting 3-methyl-6-polyisobutenyltetrahydro-benzoxazine with 3-methyl-6-tert-butyltetrahydrobenzoxazine A 500 ml evaporator bulb was initially charged with 50 g of 3-methyl-6-polyisobutenyltetrahydrobenzoxazine (based on the commercially available high-reactivity polyisobutene Glissopal® 1000 with an $M_n$ of 1000) at room temperature in 200 ml of toluene. 41 g of 3-methyl-6-tert-butyltetrahydrobenzoxazine were added rapidly. The toluene was distilled off on a rotary evaporator at 100° C./5 mbar and the mixture was stirred at 160° C./900 mbar for 4 hours. 75 g of product were obtained in the form of a viscous oil.

1H NMR (400 MHz, 16 scans, $CDCl_3$):

Based on the integral of the methyl protons (benzoxazine: 2.45-2.65 ppm; 2-hydroxy-benzylamine: 2.05-2.30 ppm), 9 phenol units are joined to one benzoxazine.

Example 6

Compound of the formula VIc by reacting 3-methyl-6-polyisobutenyltetrahydro-benzoxazine and 3-methyl-6,8-di-tert-butyltetrahydrobenzoxazine with bisphenol A In a 1000 ml four-neck flask, 130 g of 3-methyl-6-polyisobutenyltetrahydrobenzoxazine (based on the commercially available high-reactivity polyisobutene Glissopal® 1000 with an $M_n$ of 1000), 78.5 g of 3-methyl-6,8-di-tert-butyltetrahydrobenzoxazine, 22.8 g of bisphenol A and 200 ml of toluene were stirred under reflux for 2 hours. The flask contents were concentrated by evaporation at 140° C. and 5 mbar. 194.5 g of product were obtained in the form of a light, clear, viscous oil.

1H NMR (400 MHz, 16 scans, $CDCl_3$):

5% residual tetrahydrobenzoxazine signals ($\delta$=4.70 ppm, 2H, —$CH_2$—N(—$CH_3$)—$CH_2$—O—; $\delta$=3.82 ppm, 2H, —$CH_2$—N(—$CH_3$)—$CH_2$—O—) and a small residual signal for one ortho proton of bisphenol A ($\delta$=6.60 ppm) show 95% conversion; the benzyl protons are present in the range of δ=3.8-3.4 ppm, the protons of the N-methyl groups in the range of δ=2.6-2.0 ppm and the aromatic protons in the range of δ=6.7-7.3 ppm.

Example 7

Compound of the formula Vn by reacting 4-poly-isobutenylphenol with 3-(dimethylamino)propyl-6-methyl-8-tert-butyltetrahydrobenzoxazine A 1000 ml four-neck flask was initially charged with 300 g of 4-polyisobutenylphenol (based on the commercially available highly reactive polyisobutene Glissopal® 1000 with an $M_n$ of 1000) at room temperature in 190 g of Solvesso® 150 (Solvent Naphtha heavy). 145 g of 3-(dimethylamine)propyl-6-methyl-8-tert-butyltetrahydrobenzoxazine were added rapidly. The flask contents were stirred at 150° C. for 4 hours. 630 g of a light-colored, clear solution of the product (solids content 70% by weight) were obtained. For the analytical determination, a sample was concentrated by evaporation at 150° C. and 3 mbar.

1H NMR (400 MHz, 16 scans, $CDCl_3$):
Residual tetrahydrobenzoxazine signals (δ=4.80 ppm, 2H, —$CH_2$—N(—$CH_3$)—$CH_2$—O—; δ=3.91 ppm, 2H, —$CH_2$—N(—$CH_3$)—$CH_2$—O—) and a small residual signal for one ortho proton of the 4-polyisobutenylphenol (δ=6.70 ppm) show 90% conversion; the benzyl protons are present in the range of δ=3.8-3.4 ppm, the protons of the N-methyl group in the range of δ=2.6-2.0 ppm and the aromatic protons in the range of δ=6.7-7.3 ppm.

Use Examples

Example 8

Testing of the Thermal Stability of Turbine Fuel

Jet Fuel

A turbine fuel of the specification Jet A-1 according to DEF STAN 91-91 and ASTM D 1655 was used. The additization was effected in each case with 100 mg/l of the compounds from preparation examples 1 to 6.

In a three-neck flask which had been equipped with stirrer, reflux condenser and thermometer, 5 l of air were first passed at room temperature through 150 ml of the fuel to be examined within 1 h. Subsequently, the fuel was heated to 140° C. with an oil bath and stirred at this temperature for a further 5 h. After cooling to room temperature, the entire amount of fuel was filtered through a 0.45 μm membrane filter. Subsequently, the filter residue was determined gravimetrically after drying in a drying cabinet at 115° C. for 45 min and subsequently drying under reduced pressure in a desiccator for 2 hours:
Blank value (without additive): 8.9 mg
additized in accordance with the invention with 100 mg/l in each case of the following compounds:

| | |
|---|---|
| compound of the formula Vb (preparation example 1): | 1.8 mg |
| compound of the formula Ve (preparation example 2): | 1.0 mg |
| compound of the formula Vc (preparation example 3): | 1.0 mg |
| compound of the formula IIIv (preparation example 4): | 1.6 mg |
| compound of the formula IIIw (preparation example 5): | 2.5 mg |
| compound of the formula VIc (preparation example 6): | 1.0 mg |

The use of the additive used in accordance with the invention distinctly reduced the amount of particles formed by thermal stress on the turbine fuel.

Example 9

Improvement in the Thermal Stability of Turbine Fuel Get Fuel)

A turbine fuel based on the specification Jet A-1 according to DEF STAN 91-91 and ASTM D 1655 was used. The thermal stability was tested by the JFTOT breakpoint method according to ASTM D 3241. For unadditized turbine fuel, a value of 250° C. was determined. With fuels which had been additized with 100 mg/l in each case of an additive used in accordance with the invention and listed below, the following values were measured:

| | |
|---|---|
| compound of the formula Vb (preparation example 1): | 280° C. |
| compound of the formula Ve (preparation example 2): | 260° C. |
| compound of the formula Vc (preparation example 3): | 280° C. |

Example 10

Testing of the Water Compatibility of Turbine Fuel

The compound of the formula Vb from preparation example 1 and the same turbine fuel as in example 8 and 9 were used.

According to DIN 51415 and ASTM D 1094, the water compatibility of the turbine fuel and hence the undesired tendency to form emulsions was determined after addition of 100 mg/l of the compound of the formula Vb. To this end, 80 ml of the additized turbine fuel and 20 ml of water were agitated intensively in a defined manner. This was followed by visual assessment of the phase separation layers after in each case 1, 5, and 60 minutes. As early as 5 minutes after water addition, full separation of fuel and water was obtained; no emulsion fractions remained.

Example 11

Testing of the Water Separation Properties of Turbine Fuel

A turbine fuel of the specification Jet A-1 according to DEF STAN 91-91 and ASTM D 1655 was used. The tendency of turbine fuels with regard to their water separation properties was tested to ASTM D 3948 ("MSEP" test). The characteristic feature of these measurements is the use of a standard coalescence filter with final opacity measurement of the fuel phase. In the measurement, the additives used in accordance with the invention were tested in combination with the antioxidant 2,6-di-tert-butyl-4-methylphenol ("BHT") and the metal deactivator N,N'-disalicylidene-1,2-diaminopropane in a solvent customary for this purpose. The dosage of the additives used in accordance with the invention was in each case 215 mg/l (based on their 100% active substance content). The following ratings for the opacity behavior were determined [relative assessment scale from 0 (worst mark) to 100 (best mark)]:

| | |
|---|---|
| Blank value (without additive): | 98 |
| compound of the formula Vb (preparation example 1): | 97 |
| compound of the formula Vc (preparation example 3): | 98 |

No deteriorations in comparison with unadditized turbine fuel occurred.

What is claimed is:

1. A method comprising adding at least one polycyclic phenolic compound in light, oxygen and/or heat stabilizing amounts to a mineral oil-based product or fuel in need of light, oxygen and/or heat stabilization, wherein said at least one polycyclic phenolic compound comprises from 3 to 20 benzene rings per molecule and is obtained by a process comprising reacting a tetrahydrobenzoxazine of the general formula I

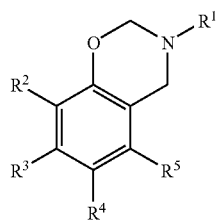
(I)

in which the substituent $R^1$ is a hydrocarbyl radical which has from 1 to 3000 carbon atoms and may be interrupted by one or more heteroatoms from the group of O and S and/or by one or more $NR^6$ moieties,
where $R^6$ is a hydrogen atom or a $C_1$- to $C_4$-alkyl radical, and
in which the substituents $R^2$, $R^3$, $R^4$ and $R^5$ are each independently hydrogen atoms, hydroxyl groups or hydrocarbyl radicals which have in each case from 1 to 3000 carbon atoms and may be interrupted by one or more heteroatoms from the group of O and S and/or by one or more $NR^6$ moieties, where $R^6$ is as defined above,
with one or more of the same or different phenols of the general formula II

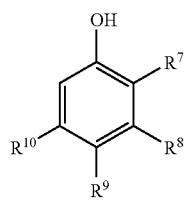
(II)

in which the substituents $R^7$, $R^8$, $R^9$ and $R^{10}$ are each independently hydrogen atoms, hydroxyl groups or hydrocarbyl radicals which have in each case from 1 to 3000 carbon atoms and may be interrupted by one or more heteroatoms from the group of O and S and/or by one or more $NR^6$ moieties, where $R^6$ is as defined above,
and/or with one or more of the same or different tetrahydrobenzoxazines of the general formula I,
where the substituent $R^4$ may also be a radical of the formula Z and the substituent $R^9$ may also be a radical of the formula Z'

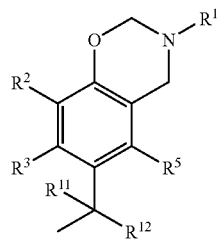
(Z)

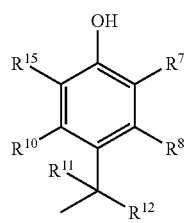
(Z')

in which the substituents $R^1$, $R^2$, $R^3$, $R^5$, $R^7$, $R^8$ and $R^{10}$ are each as defined above, the substituent $R^7$ may also be a radical derived from a tetrahydrobenzoxazine of the general formula I, the substituent $R^{15}$ is hydrogen or a radical derived from a tetrahydrobenzoxazine of the general formula I, and the substituents $R^{11}$ and $R^{12}$ may be the same or different and are each hydrogen or a $C_1$- to $C_{10}$-alkyl radical,
and in which the substituents $R^2$ and $R^3$ or $R^3$ and $R^4$ or $R^4$ and $R^5$, together with the substructure —O—CH$_2$13 NR$^{13}$—CH$_2$— attached to the benzene ring, may also form a second tetrahydrooxazine ring, or the substituents $R^2$ and $R^3$ and $R^4$ and $R^5$, together with the substructures —O—CH$_2$—NR$^{13}$—CH$_2$— and —O—CH$_2$—NR$^{14}$—CH$_2$— attached to the benzene ring, may also form a second and a third tetrahydrooxazine ring, where $R^{13}$ and $R^{14}$ are each independently hydrocarbyl radicals which have in each case from 1 to 3000 carbon atoms and may be interrupted by one or more heteroatoms from the group of O and S and/or by one or more $NR^6$ moieties, where $R^6$ is as defined above,
with the proviso that at least one of the substituents $R^1$, $R^2$, $R^3$, $R^4$, $R^5 R^7$, $R^8$, $R^9$, $R^{10}$, $R^{13}$ or $R^{14}$ is a polyisobutenyl radical having a number-average molecular weight $M_n$ of from 183 to 42 000, and the remaining substituents from the group of $R^1$, $R^2$, $R^3$, $R^4$, $R^5$, $R^7$, $R^8$, $R^9$, $R^{10}$, $R^{13}$, or $R^{14}$, when they are hydrocarbyl radicals, each have from 1 to 20 carbon atoms.

2. The method according to claim 1, in which one or two polyisobutenyl radicals having a number-average molecular weight $M_n$ of from 183 to 42 000 occur in the molecule as substituent $R^1$ and/or $R^2$ and/or $R^4$ and/or $R^7$ and/or $R^9$ and/or $R^{13}$ and/or $R^{14}$.

3. The method according to claim 1, in which the remaining substituents from the group of $R^1$, $R^2$, $R^3$, $R^5$, $R^7 R^8$, $R^9$, $R^{10}$, $R^{13}$ and $R^{14}$ which are not polyisobutenyl radicals having a number-average molecular weight $M_n$ of from 183 to 42 000 are each independently hydrogen atoms, hydroxyl groups or, when they are hydrocarbyl radicals, linear or branched $C_1$- to $C_4$-alkyl radicals.

4. The method according to claim 1, wherein said number-average molecular weight $M_n$ is from 285 to 25 000.

5. The method according to claim 1, wherein the mean polydispersity index PDI for the polyisobutenyl radicals in the polycyclic phenolic compounds is at most 5 times the mean polydispersity index/PDI for the polyisobutenyl radicals in the parent tetrahydrobenzoxazines I and/or phenols II.

6. The method according to claim 1, wherein the at least one polycyclic phenolic compound is added as an antioxidant to a turbine fuel or jet fuel.

7. The method according to claim 6, wherein the at least one polycyclic phenolic compound is added for improving the thermal stability of the turbine fuel.

8. A product produced according to the method defined in claim 1, wherein the mineral oil-based product or fuel is a turbine fuel or jet fuel.

9. The method according to claim 1, wherein the substituent $R^4$ is a radical of the formula Z.

10. The method according to claim 1, wherein the substituent $R^9$ is a radical of the formula Z'.

11. The method according to claim 1, wherein the substituent $R^4$ is a radical of the formula Z and the substituent $R^9$ is a radical of the formula Z'.

12. The method according to claim 1, in which the remaining substituents from the group of $R^1$, $R^2$, $R^3$, $R^5$, $R^7 R^8$, $R^9$, $R^{10}$, $R^{13}$ and $R^{14}$, when they are hydrocarbyl radicals, are each independently linear or branched $C_1$- to $C_4$-alkyl radicals.

* * * * *